United States Patent
Matsuura et al.

(10) Patent No.: US 11,315,774 B2
(45) Date of Patent: Apr. 26, 2022

(54) BIG-DATA ANALYZING METHOD AND MASS SPECTROMETRIC SYSTEM USING THE SAME METHOD

(71) Applicants: Shimadzu Corporation, Kyoto (JP); Teikyo University, Itabashi-ku (JP)

(72) Inventors: Masaaki Matsuura, Koto-ku (JP); Yuichiro Fujita, Kyotanabe (JP); Shigeki Kajihara, Uji (JP)

(73) Assignees: Shimadzu Corporation, Kyoto (JP); Teikyo University, Itabashi-ku (JP)

( * ) Notice: Subject to any disclaimer, the term of this patent is extended or adjusted under 35 U.S.C. 154(b) by 676 days.

(21) Appl. No.: 15/617,417

(22) Filed: Jun. 8, 2017

(65) Prior Publication Data

US 2017/0358434 A1 Dec. 14, 2017

(30) Foreign Application Priority Data

Jun. 9, 2016 (JP) .............................. JP2016-115295
Apr. 27, 2017 (JP) .............................. JP2017-088365

(51) Int. Cl.
*G01N 31/00* (2006.01)
*H01J 49/00* (2006.01)
(Continued)

(52) U.S. Cl.
CPC .......... *H01J 49/0036* (2013.01); *G01N 31/00* (2013.01); *G06F 16/287* (2019.01);
(Continued)

(58) Field of Classification Search
CPC .... H01J 49/0036; G06F 16/287; G06F 16/28; G16C 20/20; G16C 20/70; G01N 2800/7028; G01N 31/00; G16B 40/10
See application file for complete search history.

(56) References Cited

U.S. PATENT DOCUMENTS

2002/0138208 A1* 9/2002 Paulse ................ H01J 49/0036
  702/22
2006/0259246 A1* 11/2006 Huyn ..................... G16B 40/00
  702/19
(Continued)

FOREIGN PATENT DOCUMENTS

JP 2004-522980 A 7/2004
JP 2013-541697 A 11/2013
WO WO 2011/086889 A1 7/2011

OTHER PUBLICATIONS

"2011-nen Dai 12-kai Kokusai Nyuugan Gakkai Deno Nyuugan Sabutaipu No Teigi To Suishousareru Zenshin Chiryo (Subtypes of Breast Cancer Defined in the 12th Meeting of the International Breast Cancer Society, 2011, and Recommended Systematic Therapies)", The Japan Baptist Medical Foundation, The Japan Baptist Hospital, http://www.jbh.or.jp/departments/geka/policy/nyugan_chiryo.html, 3 pages.
(Continued)

*Primary Examiner* — Aleksandr Kerzhner
*Assistant Examiner* — Maher N Algibhah
(74) *Attorney, Agent, or Firm* — Oblon, McClelland, Maier & Neustadt, L.L.P.

(57) ABSTRACT

Provided is a method for sorting a number of samples into an appropriate number of clusters according to their characteristics. Highly-correlated peaks are extracted from mass spectrum data obtained for the samples (S2). Using the extracted peaks, highly-correlated sample pairs are extracted
(Continued)

(S3). While removing samples having low degrees of correlation, highly-correlated sample pairs are integrated to form core clusters (S4). Using singular peaks characterizing each core cluster, two or more core clusters are integrated to form clusters (S5-S7). These clusters include mixed clusters in which two or more clusters are mixed. Member determination formulae are created based on the singular peaks of each cluster (S8-S12). All samples, including those which have been excluded from the cluster determination process, are classified into clusters based on the member determination formulae (S14). The member determination formulae can also be used to assign a new sample to one of the cluster.

31 Claims, 15 Drawing Sheets

(51) Int. Cl.
    *G06F 16/28*     (2019.01)
    *G16C 20/70*     (2019.01)
    *G16B 40/10*     (2019.01)
    *G16C 20/20*     (2019.01)

(52) U.S. Cl.
    CPC ............ *G16B 40/10* (2019.02); *G16C 20/70* (2019.02); *G01N 2800/7028* (2013.01); *G16C 20/20* (2019.02)

(56) References Cited

U.S. PATENT DOCUMENTS

2014/0037209 A1*   2/2014   Robinson ............ G06K 9/6232
    382/170
2015/0232926 A1    8/2015   Wu et al.

OTHER PUBLICATIONS

"Jinzou Gan—Shurui To Chiryou (Kidney Cancer—Types and Symptoms)", General Medical Center for Kidney Disease, Department of Urology, Tokyo Women's Medical University, http://www.twmu.ac.jp/KC/Urology/disease/cancer/kidney/, 3 pages.

Therese Sorlie, et al. "Gene expression patterns of breast carcinomas distinguish tumor subclasses with clinical implications", Proceedings of the National Academy of Sciences of the United States of America, 2001, vol. 98, No. 19, 6 pages.

Marco Gerlinger, et al. "Intratumor Heterogeneity and Branched Evolution Revealed by Multiregion Sequencing", The New England Journal of Medicine, 2012, vol. 366, No.10, 10 pages.

Notice of Reasons for Refusal dated May 11, 2021 in Japanese Patent Application No. 2017-088365 (with English language translation), 10 pages.

Second Office Action dated Feb. 8, 2022 in corresponding Japanese Application No. 2017-088365 (with Machine Translation).

* cited by examiner

Fig. 5

| | REMOVED FROM SINGULAR PEAKS | | | | | |
|---|---|---|---|---|---|---|
| CORE CLUSTER #1 | 120.1 | 123.5 | 134.2 | 157.1 | | 175.9 |
| CORE CLUSTER #2 | | 123.5 | 134.2 | 157.1 | 168.4 | 175.9 |
| CORE CLUSTER #3 | | | 134.2 | | 168.4 | 175.9 |
| CORE CLUSTER #4 | | | | 157.1 | 168.4 | 175.9 |
| NUMBER OF COMMON PEAKS | 0 | 1 | 2 | 2 | 2 | 3 |
| REEVALUATION RESULT | NG | NG | OK | OK | OK | OK |

Fig. 6

| CORE CLUSTER | PEAK NUMBER | | | | | | | |
| | p1 | p2 | p3 | p4 | p5 | p6 | p7 ---- | pj |
|---|---|---|---|---|---|---|---|---|
| #1 | 1 | 1 | 1 | 0 | 0 | 0 | 0 ---- | |
| #2 | 1 | 1 | 1 | 0 | 0 | 0 | 0 ---- | |
| #3 | 1 | 1 | 1 | 0 | 0 | 0 | 0 ---- | |
| #4 | 0 | 0 | 0 | 1 | 1 | 1 | 0 ---- | |
| #5 | 0 | 0 | 0 | 1 | 1 | 1 | 0 ---- | |
| #6 | 0 | 0 | 0 | 1 | 1 | 0 | 0 ---- | |

1–#3: HIGHLY INTEGRATABLE
4–#5: HIGHLY INTEGRATABLE

NOTE { 1 : PEAK PRESENT
        0 : NO PEAK

Fig. 10

| PARAMETER ITEMS | VALUE |
|---|---|
| NUMBER OF SUBTYPES | 8<br>SIMPLE SUBTYPE: 5 (SUBTYPE [1]~[5])<br>MIXED SUBTYPE: 2<br>  (SUBTYPE [6]: MIXTURE OF [1] AND [3],<br>    SUBTYPE [7]: MIXTURE OF [2] AND [4])<br>SUBTYPE FOR HEALTHY INDIVIDUAL. 1 |
| TOTAL NUMBER OF SAMPLES | 800<br>100 SAMPLES PER SUBTYPE |
| NUMBER OF MARKERS PER SUBTYPE | 10 |

Fig. 11

| SUBTYPE NUMBER | PEAK NUMBER | | | | | | | | | |
|---|---|---|---|---|---|---|---|---|---|---|
| | 1 | 2 | 3 | 4 | 5 | 6 | 7 | 8 | 9 | 10 |
| 1 | 968.61 → | 1073.6 | 1123.7 | 1133.7 | ↑1405.8 | 1441.9 | 1502.8 ← | 1530.9 → | 1691 ← | 1877.1 → |
| 2 | 949.6 ← | 950.61 → | 964.6 → | ↓1073.6 | 1098.6 | ↓1123.7 | 1149.6 | 1405.8 | 1433.8 → | 1841.1 ← |
| 3 | 811.52 → | 947.61 | 965.61 ↑ | ↑1006.6 | ↓1073.6 | 1123.7 | 1050.7 | 1405.8 | 1428 ← | 1834 |
| 4 | 963.59 ← | 966.62 → | 1035.6 | ↓1073.6 | 1121.7 | ↑1073.6 | 1405.8 | 1465.8 | 1679 → | 1882.1 ← |
| 5 | 807.54 → | 837.54 | 859.55 → | 916.61 | 948.63 ← | ↑1073.6 | 1123.7 | 1279.8 | 1405.8 | 1406.9 ← |
| 6 | 811.52(3) → | 947.61(3) ↓ | 965.61(3) ↑ | 968.61(1) ↓ | 1006.6(3) ↑ | 1073.6 ↓ | 1123.7 | 1133.7(1) ↑ | 1150.7(3) ↑ | 1405.8 |
| 7 | 949.6(2) ↑ | 950.61(2) ↓ | 963.59(4) ↓ | 964.6(2) ↓ | 966.62(4) ↑ | 1035.6(4) ↓ | 1073.6 | 1098.6(2) ↑ | 1121.7(4) ↑ | 1123.7 |

| SUBTYPE NUMBER | PEAK NUMBER | | | | | | |
|---|---|---|---|---|---|---|---|
| | 11 | 12 | 13 | 14 | 15 | 16 | 17 |
| 1 | | | | | | | |
| 2 | | | | | | | |
| 3 | | | | | | | |
| 4 | | | | | | | |
| 5 | | | | | | | |
| 6 | 1428.0(3) ↑ | 1441.9(1) ↑ | 1502.8(1) ↑ | 1530.9(1) ↑ | 1691(1) ← | 1834(3) ← | 1877.1(1) ↑ |
| 7 | 1149.6(1) ↑ | 1405.8 | 1443.8(2) ↑ | 1465.8(4) ↑ | 1679(4) ↑ | 1841.1(2) → | 1882.1(4) ← |

* UNDERLINED NUMERICAL VALUES INDICATE COMMON MARKERS SHARED BY TWO OR MORE SUBTYPES.
* THE NUMBER IN BRACKETS ( ) INDICATES THAT THE PEAK IS A MARKER OF A SIMPLE SUBTYPE HAVING THAT NUMBER.

Fig. 12 m/z VALUE OF EXTRACTED PEAKS

| SUB-TYPE | | | | | | | | | | |
|---|---|---|---|---|---|---|---|---|---|---|
| 1 | 968.61 | ↓1133.7 | ↑1441.9 | ↓1502.8 | ↑1530.9 | ↓1691 | ↑1877.1 | | | |
| 2 | 949.6 | ↑950.61 | ↓964.6 | ↓1098.6 | ↓1149.6 | ↑1443.8 | →1841.1 | | | |
| 3 | 811.5 | ↓947.61 | ↓965.61 | ↑1006.6 | ↓1150.7 | ↑1428 | ↑1834 | | | |
| 4 | 963.6 | ↓966.62 | ↑1035.6 | ↓1121.7 | ↑1465.8 | ↑1679 | ↓1882.1 | | | |
| 5 | 807.5 | ↓837.54 | ↓859.55 | ↓916.61 | ↓948.63 | ↓1279.8 | ↑1406.9 | | | |
| 6 | 811.52(3)↓ | 947.61(3)↓ | 965.61(3)↑ | 968.61(1)↓ | 1006.6(3)↓ | 1035.6(4)↑ | 1133.7(1)↑ | 1150.7(3)↑ | 1405.8 | |
| 7 | 949.6(2)↑ | 950.61(2)↑ | 963.59(4)↓ | 964.6(2)↓ | 966.62(4)↑ | 1098.6(2)↓ | 1121.7(4)↓ | 1149.6(1)↑ | 1428(3) | 1443.8(2)↓ |
| 8 | 1073.6 | 1123.7 | 1405.8 | | | | | | | | m/z VALUE OF EXTRACTED PEAKS

| SUB-TYPE | | | | | | |
|---|---|---|---|---|---|---|
| 1 | | | | | | |
| 2 | | | | | | |
| 3 | | | | | | |
| 4 | | | | | | |
| 5 | | | | | | |
| 6 | 1441.9(1)↓ | 1502.8(1)↑ | 1530.9(1)↓ | 1691(1)↓ | 1834(3)↑ | 1877.1(4)↓ |
| 7 | 1465.8(4)↑ | 1679(4)↑ | 1841.1(2)→ | 1882.1(4)↑ | | |
| 8 | | | | | | |

* UNDERLINED NUMERICAL VALUES INDICATE COMMON MARKERS SHARED BY TWO OR MORE SUBTYPES.
* THE NUMBER IN BRACKETS () INDICATES THAT THE PEAK IS A MARKER OF A SIMPLE SUBTYPE HAVING THAT NUMBER.

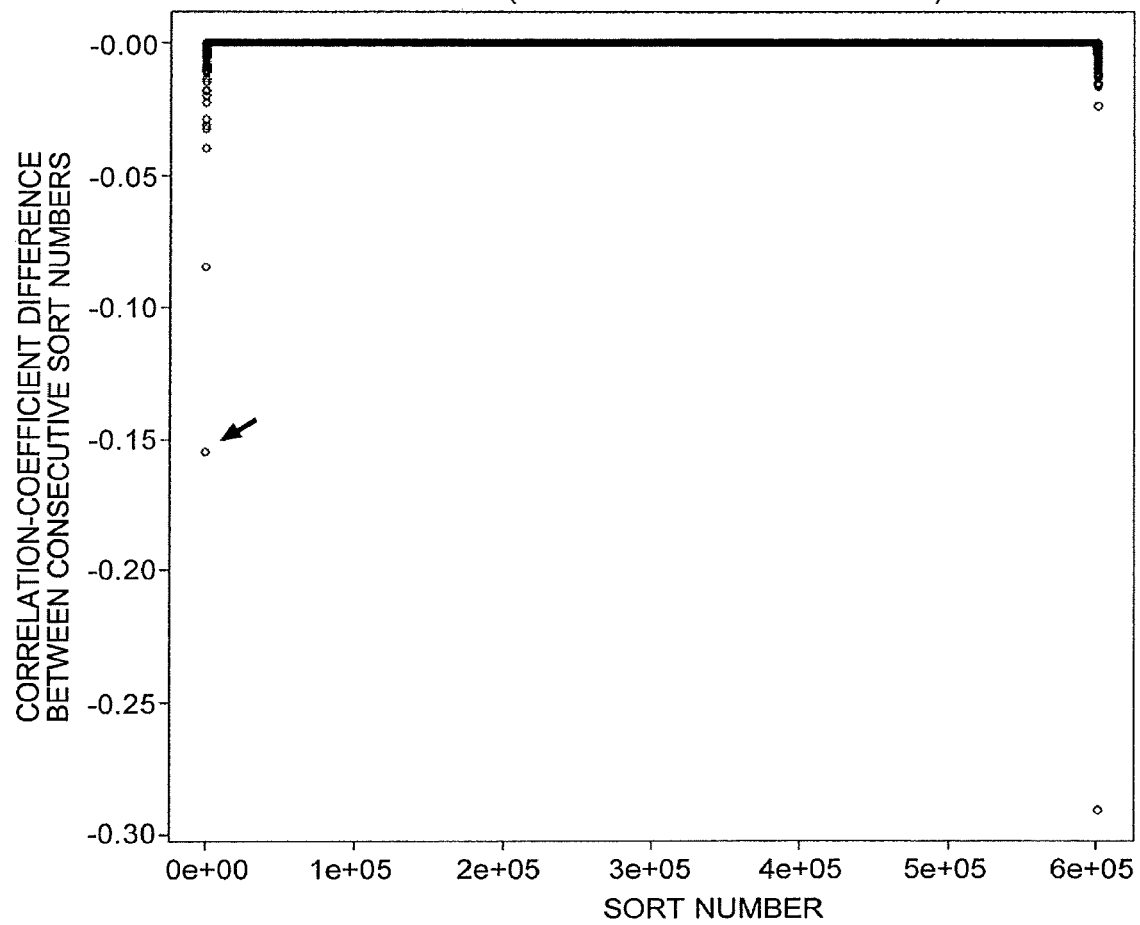

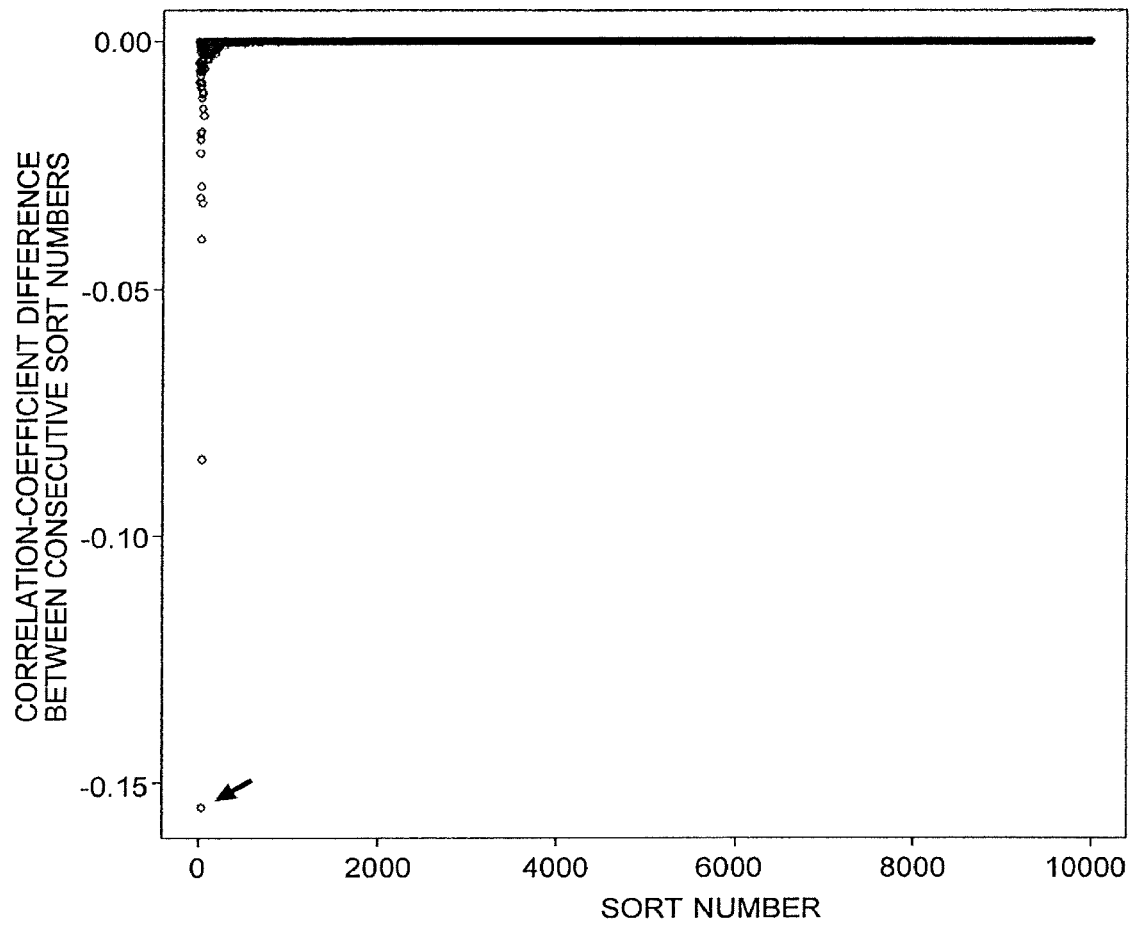

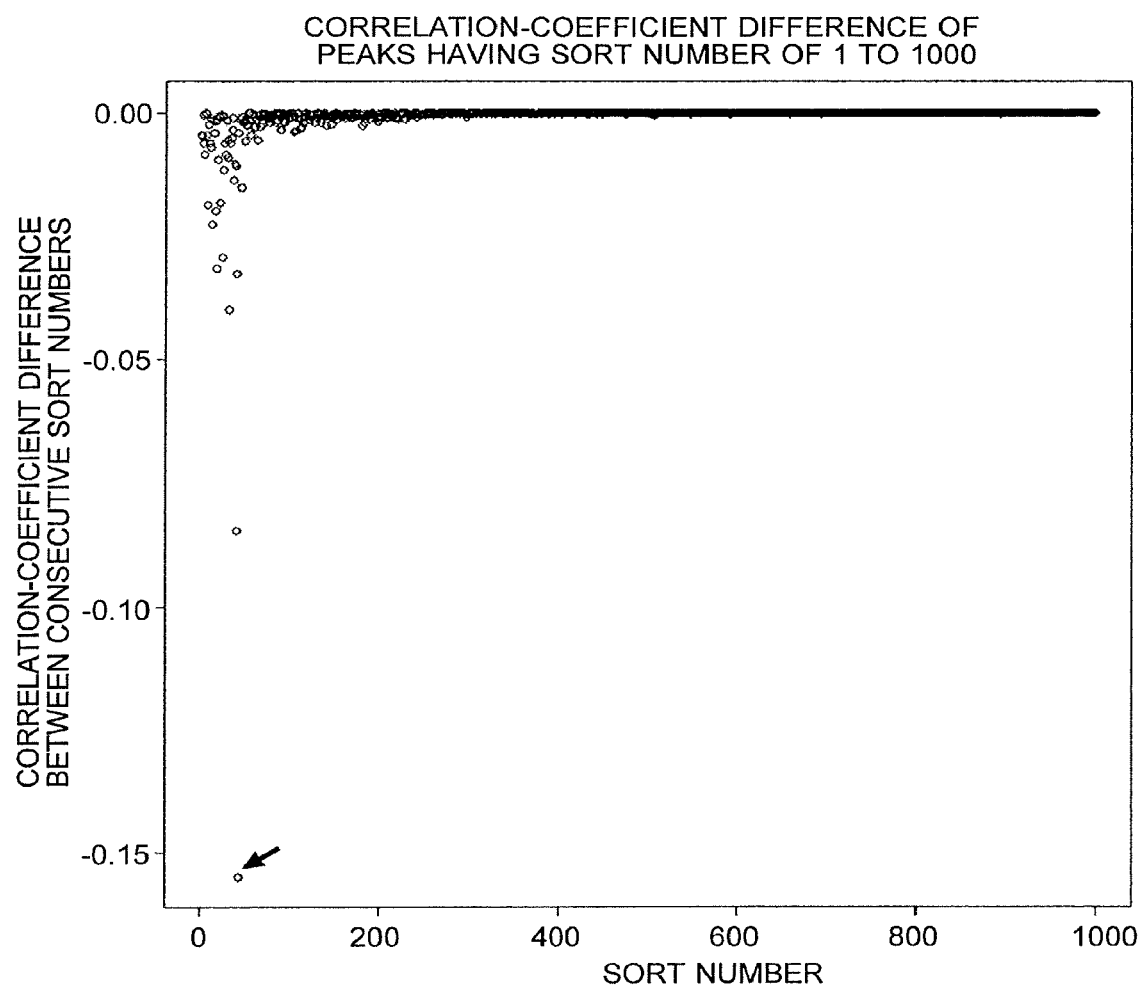

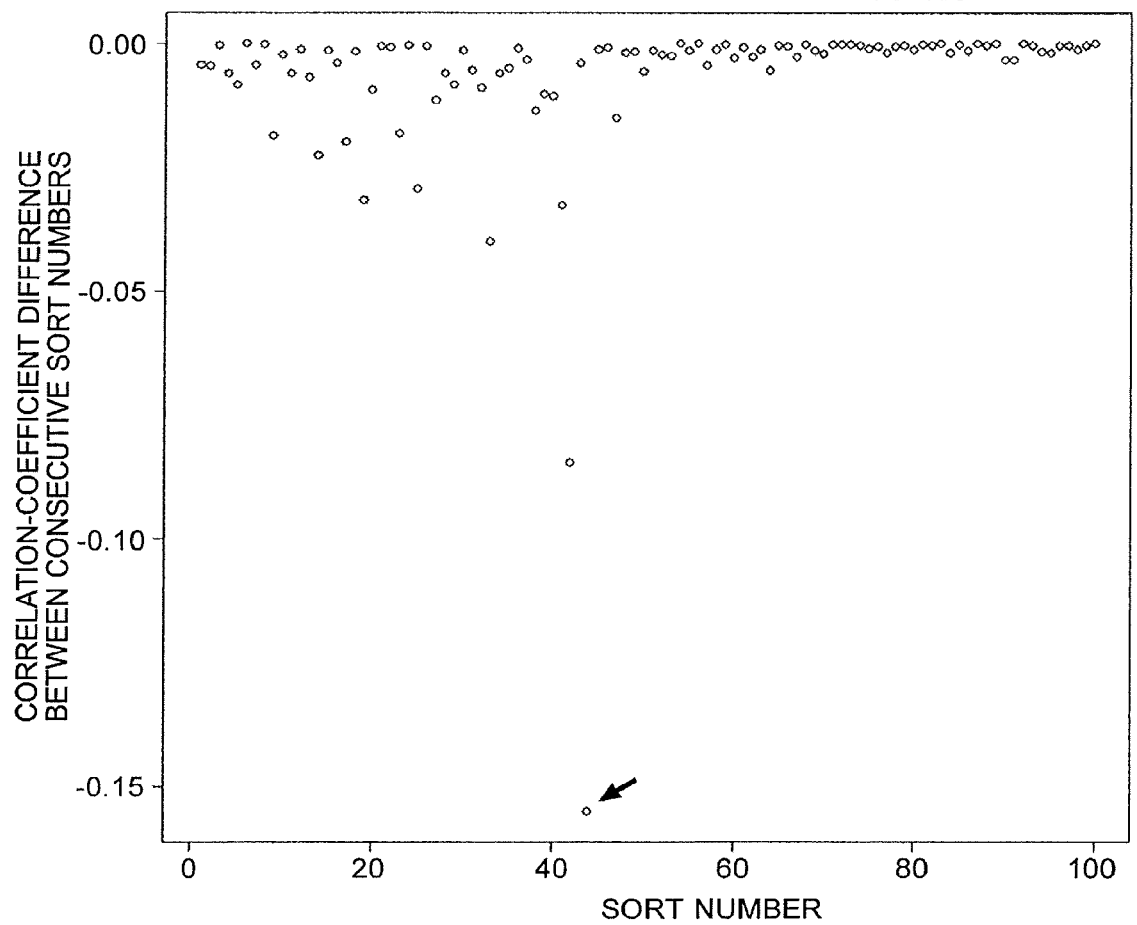

BIG-DATA ANALYZING METHOD AND MASS SPECTROMETRIC SYSTEM USING THE SAME METHOD

TECHNICAL FIELD

The present invention relates to a big-data-analyzing method for analyzing big data collected by various techniques, such as measurements, instrumentations or observations, as well as a mass spectrometric system in which this analyzing method is applied in an analysis of data obtained by mass spectrometry.

BACKGROUND ART

In recent years, cancer treatment techniques have been rapidly advancing, and various kinds of treatment drugs and methods producing higher levels of therapeutic effects than ever before have been developed. However, it goes without saying that correct diagnoses are essential to obtain high therapeutic effects. It has been commonly known that there are such types of cancer that originate from the same biological site yet can be classified into different subtypes depending on the characteristics of the cancerous cells. For example, breast cancer can be classified into Luminal A, Luminal B, Basel-like and other subtypes, as disclosed in Non Patent Literature 1. Kidney cancer is also known to have its cancerous cells classifiable into several subtypes, as disclosed in Non Patent Literature 2. As for breast cancer, it has been revealed that different subtypes require different methods and different anticancer drugs for appropriate treatments. Therapeutic efforts based on such knowledge have also been initiated. Accordingly, in a cancer diagnosis, not only the determination on whether or not the disease is due to a cancer, but also a precise diagnosis on the subtype of a detected cancer has been demanded.

Whether or not the disease is due to a cancer is normally determined by a pathological diagnosis in which a professional pathologist using a microscope observes a portion of the biological tissue sampled from the subject. As for breast cancer, the current practice for subtype determination is to perform positive/negative tests on HER2 (a kind of gene protein), ER (estrogen receptor), PgR (progesterone receptor) and other substances by immunostaining, and combine the test results to simply and approximately determine, on a clinical site, the subtype which was discovered based on the gene expression profiling using a microarray. However, even when the number of kinds of subtypes is comparatively small as in the case of breast cancer, the subtype determined by the immunostaining test on a clinical site does not always match with one of the subtypes discovered by research based on the gene expression profiling data obtained with a microarray. Accordingly, a more precise and objective method which uses biomarkers to determine the subtype has been desired.

In recent years, mass spectrometry has been frequently used for cancer diagnosis as well as other biological analyses. A mass spectrometric analysis for a sample normally yields mass spectrum data over a predetermined range of mass-to-charge ratios. On the obtained mass spectrum, a number of peaks originating from various components contained in the sample can be observed. Based on the mass-to-charge ratio values corresponding to those peaks, a component can be identified. Additionally, the signal-intensity values of those peaks allow for the quantitative determination of the component concerned. Accordingly, for example, in the case of a type of cancer which causes a specific kind of component to occur within a living organism or one which changes the amount of such a component, it is possible to detect an occurrence of that cancer as well as determine its subtype by detecting, as a singular marker, a peak which corresponds to that specific component.

Various analyzing techniques for classifying a large number of samples into clusters according to the data collected for each sample have been commonly known. They are also often used in the so-called "data mining" process. Examples of the commonly used techniques for such analyses include the hierarchical cluster analysis (HCA), partitional optimization clustering (e.g. k-means clustering) and consensus clustering. For example, Non Patent Literature 3 discloses a technique in which the subtype of breast cancer is determined by a microarray analysis, i.e. an analysis of the genes expressed in the cancerous tissue. This analysis employs the HCA to classify the sample into a plurality of subtypes. There is also a technique in which a score plot obtained by the principal component analysis (PCA) is used to classify a large number of samples into a plurality of groups. On the PCA score plot, the distance between the plotted positions which correspond to the samples represents the degree of similarity of the samples. Therefore, the samples can be grouped by the distance between their plotted positions.

However, any of those conventional analyzing methods is not always suitable for such applications as the determination of the subtype of a cancer. One major reason is the fact that a sample does not always belong to a single subtype but may possibly belong to two or more subtypes. For example, Non Patent Literature 4, which is concerned with kidney cancer, shows one case where multiple subtypes of cancerous cells were mixed with each other in a single biological tissue. Similar mixtures of two or more subtypes of cancerous cells have also been increasingly discovered in other types of cancer which occur in other sites. Accordingly, in the determination of the subtype of a cancer, it is necessary to assume that multiple subtypes of the cancer may possibly be mixed in one sample.

However, the aforementioned techniques of clustering analysis, such as the HCA, are based on the assumption that any sample can be classified into a single cluster; there is no consideration of a sample being classifiable into two or more clusters. The technique which uses the PCA score plot is also incapable of determining whether or not a sample belongs to a plurality of clusters or to another cluster different from those clusters. Thus, if there is a sample which actually belongs to a plurality of subtypes (i.e. which contains a mixture of two or more subtypes), the conventional analyzing techniques are incapable of discovering the very fact that this sample belongs to a plurality of subtypes. It is also naturally impossible to determine what subtypes are mixed in the sample.

In the case of the HCA or consensus clustering, the sample-classifying process can be performed while automatically determining an optimum number of clusters, without requiring the number of clusters to be initially specified. However, the process still requires an analysis operator to give some instructions or perform some setting for the determination of the optimum number of clusters, so that there is room for subjective judgments by the analysis operator. Therefore, it is not guaranteed that the task of classifying samples into clusters is always precisely performed by consistent criteria. Additionally, in the HCA or some other techniques, the cluster formation can be more definite with an increase in the number of markers which characterize each cluster (in the case of using mass spectrum data, the number of singular peaks) or an increase in the difference in the intensities of those markers. In other words, accurate clustering may be impossible if there is only a small number of markers or if those markers have a small intensity difference.

In order to enable the determination of the cluster assignment for a new sample which is not included in a large number of samples originally used for defining the clusters, it is necessary to specify characteristic markers for each cluster. Needless to say, if the clustering is inappropriate, it is difficult to specify highly reliable markers, and if the markers are unreliable, it is difficult to correctly sort new samples into clusters. Even when the clustering is accurate, an extraction of appropriate markers may be impossible, or the extracted markers may be inaccurate, if the conditions of the markers are complex, as in the case where some of the markers are shared by a plurality of clusters (e.g. there is a marker whose quantity singularly increases in both cluster X and cluster Y) or the case where there is a cluster having a plurality of markers in which one marker appears in a larger quantity than in the other clusters while another marker appears in a smaller quantity, or if the total number of clusters is considerably large.

Needless to say, the previously described kind of problem is not unique to the determination of the subtype of a cancer. The need for classifying a large number of samples into characteristic groups based on a set of data obtained by a measurement, instrumentation, observation or the like performed for each sample has been generally recognized in various areas. For example, in the areas of medical treatment, drug development and life science which deal with biological samples, various analyses which are collectively called the "omics" analysis are performed, such as the genomic analysis, proteome analysis, metabolome analysis, interactome analysis and cellome analysis. In these areas, it is necessary to divide a large number of samples into groups based on the data collected by various analyses and measurements (which are not limited to mass spectrometry), and additionally, to investigate which group a new sample belongs to. The need for dividing a large number of samples into groups also frequently arises in an analysis of various kinds of image data, such as the mass spectrometric imaging image, radiographic image or fluorescence image.

A similar data analyzing technique may also be required in different areas from the instrumental analysis, e.g. in a variety of data analyses called the "big-data analysis" or "data mining", such as the marketing data analysis, logistics data analysis, data analysis for quality control or abnormality detection, financial data analysis or meteorological data analysis.

CITATION LIST

Non Patent Literature

Non Patent Literature 1: "2011-nen Dai 12-kai Kokusai Nyuugan Gakkai Deno Nyuugan Sabutaipu No Teigi To Suishousareru Zenshin Chiryo (Subtypes of Breast Cancer Defined in the 12th Meeting of the International Breast Cancer Society, 2011, and Recommended Systematic Therapies)", [online], The Japan Baptist Medical Foundation The Japan Baptist Hospital, [accessed on Jan. 18, 2016], the Internet Non Patent Literature 2: "Jinzou Gan—Shurui To Chiryou (Kidney Cancer—Types and Symptoms)", [online], Tokyo Joshi Ika Daigaku Hinyouki-ka Jinzoubyou Sougou Iryou Sentaa (General Medical Center for Kidney Disease, Department of Urology, Tokyo Women's Medical University), [accessed on Jan. 18, 2016], the Internet Non Patent Literature 3: T. Sorlie and 16 other authors, "Gene expression patterns of breast carcinomas distinguish tumor subclasses with clinical implications", *Proceedings of the National Academy of Sciences of the United States of America*, Sep. 11, 2001, Vol. 98, No. 19, pp. 10869-10874

Non Patent Literature 4: M. Gerlinger et al., "Intratumor Heterogeneity and Branched Evolution Revealed by Multiregion Sequencing", *The New England Journal of Medicine*, Mar. 8, 2012, Vol. 366, No. 10, pp. 883-892

SUMMARY OF INVENTION

Technical Problem

In summary, when a large number of samples need to be divided into groups as in the aforementioned case of the cancer subtype classification, the following requirements must be satisfied:

(1) A portion or the entirety of the samples can be properly divided into clusters even when there is a sample which simultaneously belongs to two or more clusters, or in other words, even when there is a cluster which is a mixture of two or more clusters.

(2) Samples can be divided into clusters whose number is appropriately determined based on quantitative and objective indices or criteria, without relying on subjective judgements by analysis operators.

(3) Highly reliable markers can be extracted for each cluster even if the number of extracted clusters is different from the actual number of clusters.

(4) An appropriate clustering and highly reliable marker extraction can be achieved even when the conditions of the markers are complex, the number of markers is insufficient, the difference in the intensities of the markers among the samples is to a certain extent small, and/or the number of clusters is large.

(5) Not only the classification of a large number of samples into clusters, but also a highly reliable judgment on the cluster assignment for a newly and separately obtained sample can be achieved.

The present invention has been developed to solve the previously described problems. One of its objectives is to provide a big-data analyzing method capable of satisfying various aforementioned requirements.

Another objective of the present invention is to provide a mass spectrometric system capable of conveniently determining, with a high degree of reliability, which cluster a sample that was not used in the learning process belongs to among a plurality of previously set clusters.

Solution to Problem

The big-data analyzing method according to the present invention developed for solving the previously described problem is a method for analyzing data including, as one item of information, quantitative values with respect to a plurality of variable values for each of a plurality of samples, the method including:

a) a cluster determination step, in which, for all samples, the degree of similarity between the samples is determined and a plurality of clusters are determined by grouping samples which are estimated to have comparatively high degrees of similarity into each cluster while excluding a sample which is estimated to have a comparatively low degree of similarity with any of the other samples;

b) a marker designation step, in which, in each of the plurality of clusters, one or more variable values characterizing the cluster concerned are designated as a marker or markers; and c) a judgment information creation step, in which, in each of the plurality of clusters, judgment information for determining whether or not a sample belongs to the cluster concerned based on the marker or markers designated in the marker designation step is created, where, for a given sample, one or more clusters which the sample may possibly belong to can be determined based on the judgment information corresponding to each of the plurality of clusters.

The "data including, as one item of information, quantitative values with respect to a plurality of variable values for each of a plurality of samples" are a collection of data that can be expressed in the form of a matrix holding quantitative values as its elements arranged in rows and columns, with the variable values as one parameter arranged in one of the row and column directions and the sample identifiers (e.g. sample names, sample numbers, etc.) as another parameter arranged in the other direction.

Specifically, for example, in the case of analyzing mass spectrum data obtained by a mass spectrometric analysis performed on a sample, the plurality of variable values are mass-to-charge ratio values, while the quantitative values are signal intensity values.

In the case of a microarray analysis, the plurality of variable values are the names of the gene probe set on the microarray, while the quantitative values are expression levels.

In the conventional and common cluster analyses, including the HCA, a plurality of clusters are determined so that each of all samples being analyzed belongs to one of the clusters. In other words, all samples are divided into groups by drawing boundaries among those samples. By comparison, in the cluster determination step of the big-data analyzing method according to the present invention, all samples being analyzed are filtered in such a manner that samples which are highly certain to have similar data are maintained while a sample which seems to be similar to none of the other samples is excluded from the task of determining the clusters. As a result, each cluster is determined based on a limited set of samples which are estimated to have high degrees of similarity.

In the marker designation step, in each of the clusters determined in the previously described manner, one or more variable values characterizing the cluster are designated as the markers. For example, in this marker designation step, a significant-difference test (e.g. t-test) on the quantitative values corresponding to the same variable value may be performed between the samples included in one cluster and the samples which are not included in this cluster, and the markers may be designated based on the test result (e.g. the p-value calculated in the t-test). Examples of the methods available for the significant-difference test include Welch's t-test, Student's t-test, and Wilcoxon rank sum test.

In the judgment information creation step, in each of the plurality of clusters, a piece of judgment information for determining whether or not a sample belongs to the cluster concerned based on the marker or markers designated in the marker designation step is created. For example, the judgment information for a cluster may be a judgment formula which takes a set of sample data (i.e. quantitative values of one or more markers) as input and yields an estimated probability with which the sample belongs to the cluster concerned. In this manner, a plurality of clusters can be determined based on a large number of samples being analyzed. For each of those clusters, one or more characterizing markers can be extracted, and based on those markers, a piece of information which is usable for determining whether or not a given sample belongs to the cluster concerned can be created.

For example, consider the case where there are two or more samples which all possess the characteristics of two different clusters A and B. Such samples should be judged to belong to both clusters. However, in the clustering process by the conventional cluster analyzing methods, each of those samples is forced to belong to either cluster A or B from the viewpoint of which of the two clusters A and B is closer to the sample. By comparison, in the clustering process by the big-data analyzing method according to the present invention, it is likely that such samples are judged to be similar to each of the two clusters A and B yet with a low degree of certainty, so that a new cluster different from clusters A and B will be created for those samples. As a result, a separate cluster which exhibits a mixture of the characteristics of two or more clusters is created.

In the big-data analyzing method according to the present invention, for example, in the cluster determination step, the plurality of clusters may be determined in such a manner that a sample pair formed by two samples which are estimated to have a high degree of similarity of data with a high degree of certainty are used as a nucleus, and other samples which are estimated to have a high degree of similarity with one of the two samples are aggregated around the nucleus.

The process of searching for a sample pair can be performed as follows: the degree of similarity of the quantitative values corresponding to different variable values in each sample is judged to extract variable values which have a high degree of similarity with each other in the sample, and the sample pair is searched for based on the degree of similarity of the extracted variable values among the samples.

Both the index for measuring the degree of similarity of the quantitative values corresponding to different variable values and the index for measuring the degree of similarity of the variable values between the samples should preferably have a quantitative nature. As a typical example, the correlation coefficient can be used. In this case, if the correlation coefficient of the quantitative values corresponding to different variable values in each sample (e.g. the correlation coefficient between the peaks corresponding to different mass-to-charge ratios) is equal to or higher than a first preset threshold, the two quantitative values can be judged to have a satisfactory degree of similarity, and additionally, if the correlation coefficient of the extracted variable values between two samples (e.g. the correlation coefficient of the mass-to-charge ratios between two samples) is equal to or higher than a second preset threshold, the two samples can be used as a sample pair. The first and second thresholds should preferably have appropriately adjustable values.

In the cluster determination step of the big-data analyzing method according to the present invention, the degree of similarity may be judged for each of the sample pairs formed by all possible combinations of two samples, and a representative sample pair to be used as a new nucleus may be designated in descending order of the degree of similarity of the sample pairs (e.g. in descending order of the correlation coefficient mentioned earlier) under the condition that the sample pair concerned are not a member of any of the clusters already selected as nuclei, while a sample pair having one sample included in a cluster already selected as a nucleus are aggregated into the same group as the representative sample pair to form a core cluster which becomes an origin of a cluster.

In one mode of the present invention, after the core clusters are formed in the previously described manner, in each of the core clusters a plurality of variable values characterizing the core cluster are designated as the markers, and if there are two or more core clusters which have common markers by a proportion equal to or higher than a predetermined value, these two or more core clusters are integrated into one cluster.

After the core-cluster formation process is completed, if there is a sample pair which has not been grouped with any other sample pair, the samples included in that sample pair can be excluded from the cluster determination process, as with the samples which have not been paired with any other sample.

In this manner, highly reliable core clusters are initially formed based on highly correlated sample pairs, and a plurality of core clusters are subsequently integrated into one cluster. By such a process, samples having comparatively low degrees of similarity of data are filtered out, so that clusters which selectively include samples having high degrees of similarity of data with a high degree of certainty can be formed.

In the big-data analyzing method according to the present invention, whether or not one cluster is a mixture of two other clusters can be determined based on the number of markers commonly included in the cluster concerned and in each of the two other clusters. By this method, a sample which possesses combined characteristics of a plurality of clusters can be properly classified into a cluster different from those plurality of clusters. Additionally, the clusters whose characteristics are possessed by that sample can also be identified.

In the judgment information creation step of the big-data analyzing method according to the present invention, a calculating formula for calculating a sample's probability of being assigned to a cluster by performing a logistic regression analysis on the quantitative values of a plurality of markers designated for the cluster may be determined as the judgment information for each cluster.

In order to improve the accuracy of the judgment information, it is preferable to test the judgment information determined for each cluster to see whether or not the assignment of the samples in the cluster is correctly judged based on the judgment information, and perform a feedback process based on the test result. Accordingly, in a preferable mode of the big-data analyzing method according to the present invention, whether or not a portion or the entirety of the samples included in each cluster belong to the cluster concerned is determined based on the judgment information created in the judgment information creation step, and if there is a sample which is unlikely to belong to the cluster concerned, the process of designating a marker or markers characterizing the cluster concerned and creating the judgment information based on the marker or markers is once more performed after the aforementioned sample is removed from the cluster concerned. Needless to say, such a process may be repeatedly executed multiple times, although a single execution is practically sufficient.

At the point in time where the judgment information for each cluster has been determined in the previously described manner, the samples which have been judged as being included in none of the clusters and therefore excluded from the process remain unassigned. Accordingly, the big-data analyzing method according to the present invention may further include a sample-classifying step in which any sample that is one of all samples yet included in none of the clusters at any stage before the eventual determination of the judgment information is assigned to one of the clusters, based on the judgment information determined for each cluster. By this method, every sample being analyzed can be classified to one of the clusters (inclusive of a cluster which is a mixture of two or more different clusters).

As noted earlier, the correlation coefficient may be used as the index for measuring the degree of similarity of the quantitative values corresponding to different variable values. In this case, as one mode of the present invention, the big-data analyzing method may further include:

a correlation coefficient calculation step, in which the correlation coefficient between all quantitative values corresponding to different variable values is calculated for every possible pair of the variable values;

a correlation-coefficient difference calculation step, in which all correlation coefficients obtained by calculation are arranged in order of the value of the correlation coefficient, and the difference between each neighboring pair of the correlation coefficients is calculated; and a threshold determination step, in which the amount of change in the difference between each neighboring pair of the correlation coefficients is sequentially calculated in order of the value of the correlation coefficient, and a threshold for judging the degree of similarity of the quantitative values is determined based on the amount of change, where, in the cluster determination step, the degree of similarity of the quantitative values corresponding to different variable values in each sample is judged using the threshold determined in the threshold determination step, to extract variable values having a high degree of similarity.

In general, it is possible to consider that quantitative values corresponding to variable values which characterize the same cluster, i.e. which can be designated as markers for the cluster, have a high degree of correlation with each other, while quantitative values corresponding to non-characteristic variable values have a low degree of correlation with each other. Therefore, the correlation coefficients calculated in the correlation coefficient calculation step tend to form two major groups, i.e. one group formed by correlation coefficients having comparatively large absolute values (close to one) and being close to each other, and another group formed by correlation coefficients having comparatively small absolute values (close to zero) and being close to each other, with only a small number of correlation coefficients located between these two groups. Accordingly, when all correlation coefficients are arranged in order of their values and the difference between each neighboring pair of the correlation coefficients is calculated by the correlation-coefficient difference calculation step, a significant difference in the correlation coefficient occurs between the two aforementioned groups. Therefore, in the threshold determination step, the amount of change in the difference between each neighboring pair of the correlation coefficients is sequentially calculated in order of the value of the correlation coefficient, and a correlation coefficient at which a significant change occurs, i.e. at which there is a significant difference between the neighboring correlation coefficients, is located, whereby an appropriate threshold for judging the degree of similarity of the quantitative values is determined.

In the case of using the correlation coefficient as the index for measuring the degree of similarity of the variable values between the samples, the previously described technique can be similarly use to determine the threshold. That is to say, as another mode of the big-data analyzing method according to the present invention, the method may further include:

a correlation coefficient calculation step, in which the correlation coefficient of the variable values between the samples is calculated for every possible pair of the samples;

a correlation-coefficient difference calculation step, in which all correlation coefficients obtained by calculation are arranged in order of the value of the correlation coefficient, and the difference between each neighboring pair of the correlation coefficients is calculated; and a threshold determination step, in which the amount of change in the difference between each neighboring pair of the correlation coefficients is sequentially calculated in order of the value of the correlation coefficient, and a threshold for judging the degree of similarity of the variable values between the samples is determined based on the amount of change, where, in the cluster determination step, the degree of similarity of the variable values between the samples is judged using the threshold determined in the threshold determination step, to extract samples having a high degree of similarity.

By these modes of the present invention, it is possible to automatically determine an appropriate threshold which is used when the degree of similarity between the quantitative values corresponding to different variable values or the degree of similarity of the variable values between the samples is judged based on the correlation coefficient.

In the previously described mode of the big-data analyzing method according to the present invention, the threshold determination step may specifically be configured so that the correlation coefficients are sorted in ascending or descending order and labeled with sort numbers, and the threshold is determined using a correlation-coefficient difference distribution chart having two orthogonally intersecting axes, with one axis indicating the sort number and the other axis indicating the difference between two correlation coefficients having consecutive sort numbers. On this correlation-coefficient difference distribution chart, if there is a single correlation-coefficient difference which is outstanding in the direction in which the absolute value of the correlation-coefficient difference increases, the threshold can be determined based on the correlation coefficient which gives this outstanding correlation-coefficient difference. The presence of an outstanding single correlation-coefficient difference in the aforementioned direction indicates that there is an extremely large difference in correlation coefficient between the consecutive sort numbers. Accordingly, it is possible to consider that whether or not there is a high degree of similarity in the quantitative values can be determined with a high degree of certainty by using the threshold determined at or around the outstanding point.

If no such outstanding correlation-coefficient difference can be located, the threshold can be determined by choosing, on the correlation-coefficient difference distribution chart, a correlation coefficient corresponding to the sort number at which the distribution of the correlation-coefficient difference along the axis indicating the sort number exhibits a convex form bulging in the direction in which the absolute value of the correlation-coefficient difference increases.

By using the correlation-coefficient difference distribution chart in the previously described manner, a correlation coefficient at which the largest change occurs in the correlation-coefficient difference sequentially calculated in order of the value of the correlation coefficient can be easily located.

In the threshold determination step in the previously described mode of the big-data analyzing method according to the present invention, the correlation coefficient corresponding to a tip position of the convex portion on the correlation-coefficient difference distribution chart can be chosen as the threshold.

The tip position of the convex portion is the position where the correlation coefficients sorted in descending or ascending order shows the largest change. Accordingly, the threshold determined in the previously described manner can be considered to be an optimum threshold as the boundary of the two aforementioned groups each of which is formed by correlation coefficients having close values.

In the threshold determination step in the previously described mode of the big-data analyzing method according to the present invention, a correlation coefficient corresponding to an extremum of a fitting curve represented by a predetermined function which fits to the convex portion on the correlation-coefficient difference distribution chart may be chosen as the threshold.

In the threshold determination step in the previously described mode of the big-data analyzing method according to the present invention, for example, whether or not the convex portion is present may be determined based on a change in the density of the plotted data points on the correlation-coefficient difference distribution chart.

In the previously described mode of the big-data analyzing method according to the present invention, a correlation coefficient corresponding to a position displaced from the tip position within the convex portion of the distribution of the correlation-coefficient difference on the correlation-coefficient difference distribution chart may be chosen as the threshold, other than the threshold determined in the previously described manner by choosing the correlation coefficient corresponding to the tip position of the convex portion. According to this mode of the present invention, it is possible to intentionally set a higher threshold for judging the correlation coefficient, i.e. to apply a stricter criterion for the selection of the markers or samples, so as to prevent a mixture of inappropriate markers or samples, or conversely, to intentionally set a lower threshold for judging the correlation coefficient, i.e. to apply a less strict criterion for the selection of the markers or samples, so as to maximally avoid an omission of the markers or samples. Thus, the reliability of the selected data can be adjusted according to the purpose of the analysis.

In the previously described mode of the big-data analyzing method according to the present invention, the correlation-coefficient difference distribution chart may be displayed on a screen of a display unit. In that case, the threshold determined in the threshold determination step may preferably be highlighted on the correlation-coefficient difference distribution chart displayed on the display unit. This allows users to intuitively grasp the state of distribution of the correlation coefficients in which the threshold has been automatically determined.

In the previously described mode of the big-data analyzing method according to the present invention, the threshold determined in the threshold determination step may be modified, or the threshold may be directly determined, according to a user instruction on the correlation-coefficient difference distribution chart displayed on the display unit. This allows users to easily modify the threshold when, for example, the user has judged that the automatically determined threshold is inappropriate. It also conveniently allows manual setting of the threshold instead of the automatic setting.

In the previously described mode of the big-data analyzing method according to the present invention, for example, when there is not a sufficient number of markers characterizing a cluster in the data being analyzed, or when there is a sufficient number of markers but their signal intensities are insufficient, it is possible that neither a single outstanding correlation-coefficient difference nor a convex distribution of the correlation-coefficient difference is observed on the correlation-coefficient difference distribution chart. In such a case, it is highly likely that the formation of the clusters, determination on the assignment of a sample to one of the clusters or other operations by the big-data analyzing method according to the present invention are unreliable. Accordingly, in the previously described mode of the big-data analyzing method according to the present invention, the determination on the assignment of a sample to a cluster by the analyzing method may be verified based on a distribution shape on the correlation-coefficient difference distribution chart.

Specifically, for example, the user may be allowed to visually check whether or not a single outstanding correlation-coefficient difference and a convex distribution of the correlation-coefficient difference are observed on the distribution shape of the correlation-coefficient difference. If neither of these features is observed, the user can determine that the analyzing method according to the present invention is unreliable, and if those features are observed, the user can determine that the analyzing method according to the present invention is reliable. Thus, the user can determine whether or not the use of the big-data analyzing method according to the present invention is appropriate in the first place.

The big-data analyzing method according to the present invention can be used in an application in which the sample is a biological sample, and the subtype of a specific kind of cancer is determined by analyzing mass spectrum data obtained by performing a mass spectrometric analysis on the sample.

By this mode of the method, the subtype of a cancer which is a mixture of two or more subtypes can be appropriately determined. Such a determination has been difficult by conventional analyzing techniques. Thus, an appropriate treatment for a specific subtype of cancer can be performed.

A mass spectrometric system according to the present invention is a mass spectrometric system employing the big-data analyzing method according to the present invention to analyze data, the system including:

a mass spectrometry executer for performing a mass spectrometric analysis on a target sample to obtain mass spectrum data;

an information storage section in which the judgment information determined in the judgment information creation step is previously stored;

a judgment processor for making a judgment by applying, to the judgment information stored in the information storage section, the mass spectrum data obtained with the mass spectrometry executer, and for determining a cluster which the target sample should be assigned to or yielding useful information for the determination of the assignment, based on the result of the judgment; and a result output section for visually providing users with a process result obtained with the judgment processor.

In the mass spectrometric system according to the present invention, for example, the judgment information stored in the information storage section may be previously prepared for specific purposes, such as the diagnosis of a cancer in a specific site, by a manufacturer of the present mass spectrometric system and stored in a memory or similar storage. Alternatively, the judgment information may be prepared as a portion of a data processing application software product for a specific purpose and offered to users by a system manufacturer or software developer. An example of the result output section is a display unit having a display screen on which the process result is displayed in a table format or any appropriate format internally determined by the system or previously specified by a user.

By using the mass spectrometric system according to the present invention, users can conveniently obtain information on one or more clusters which a target sample belongs to.

Advantageous Effects of the Invention

The big-data analyzing method according to the present invention produces the following effects:

(1) Even a sample having the characteristics of two or more clusters can be classified into an appropriate cluster, not to mention a sample that is classifiable into a single cluster.

(2) Samples can be classified into an appropriate number of clusters determined based on a quantitative and objective index, without requiring the number of clusters to be previously specified as well as without relying on a subjective judgment by an analysis operator.

(3) Since the samples sorted into each cluster during the cluster determination process are considerably similar to each other, highly reliable markers can be extracted for each cluster regardless of the number of clusters. Furthermore, an appropriate cluster formation and highly reliable marker extraction can be achieved even if the conditions of the markers are complex, the number of markers is insufficient, the difference in the intensity of the markers between samples is to some extent small, or a large number of clusters are present.

(4) Not only the classification of a large number of prepared samples into clusters, but also a highly reliable determination of a cluster which a new sample should belong to can be achieved.

(5) In most of the conventionally known big-data analyzing techniques including neural networks, the analysis is normally performed by a high-performance computer designed for scientific calculations, consuming considerable amounts of time. By comparison, the big-data analyzing method according to the present invention employs statistical techniques which merely involve simple calculations, such as the correlation-coefficient calculation or logistic regression analysis. Therefore, the process can be satisfactorily performed on commonly used personal computers (PC), which reduces the analyzing cost. Additionally, users can easily attempt an analysis using a personal computer at hand.

BRIEF DESCRIPTION OF DRAWINGS

FIG. 5 is a model diagram for explaining a process for reevaluating singular peaks in specific core clusters in the big-data analyzing method of the present embodiment.

FIG. 6 is a table illustrating a process for investigating the integratability of the core clusters in the big-data analyzing method of the present embodiment.

FIG. 10 is a table showing the peak information creation conditions under which a computation for confirming the effect of the big-data analyzing method of the present embodiment was performed.

FIG. 11 is a table showing a list of m/z values of the peaks chosen in a calculation performed for confirming the effect of the big-data analyzing method of the present embodiment.

FIG. 12 is a table showing a list of m/z values of the peaks for each subtype, obtained as a result of the big-data analyzing method of the present embodiment.

FIG. 15 is a chart illustrating the process for automatically determining the threshold for judging the correlation coefficient shown in FIG. 13.

FIG. 16 is a chart illustrating the process for automatically determining the threshold for judging the correlation coefficient shown in FIG. 13.

FIG. 17 is a chart illustrating the process for automatically determining the threshold for judging the correlation coefficient shown in FIG. 13.

FIG. 18 is a chart illustrating the process for automatically determining the threshold for judging the correlation coefficient shown in FIG. 13.

DESCRIPTION OF EMBODIMENTS

[Description of Data Analyzing Method (CCD Method)]

Figure 1:
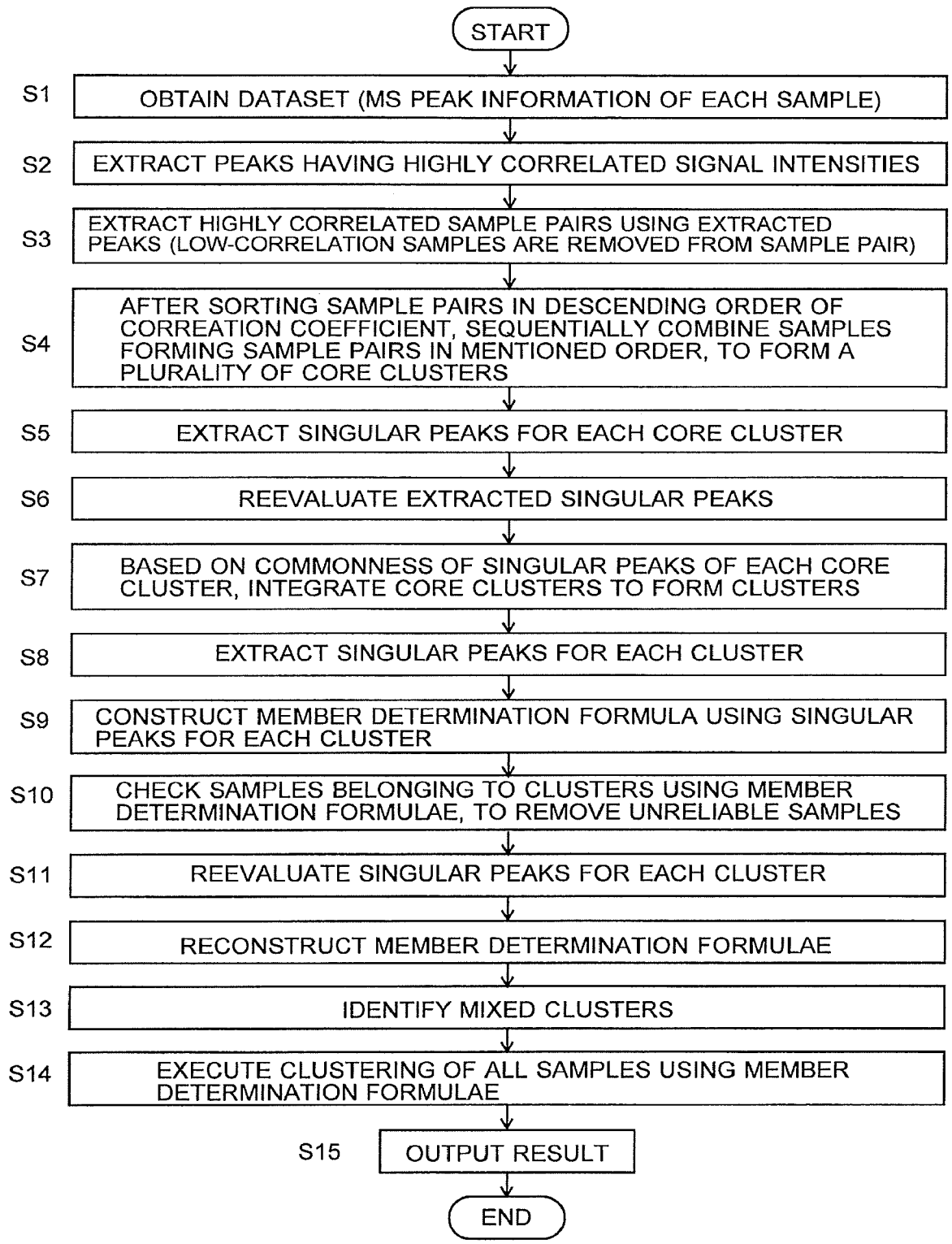
FIG. 1 is a flowchart showing an analyzing procedure in a big-data analyzing method as one embodiment of the present invention.

Initially, a big-data analyzing method as one embodiment of the present invention is described with reference to the attached drawings. FIG. 1 is a flowchart showing the analyzing procedure in the big-data analyzing method of the present embodiment. In the following descriptions, the big-data analyzing method of the present embodiment will be called the CCD (core cluster detection) method. The reason for using such a name will naturally be clarified with the following descriptions.

Hereinafter considered is the case where biological samples (e.g. cancerous tissues) taken from a large number of cancer patients and healthy individuals are treated as samples, and the big-data analyzing method of the present embodiment, i.e. the CCD method, is used in order to classify the cancer into subtypes as well as determine which subtype each sample belongs to, based on mass spectrum information obtained by a mass spectrometric analysis of the samples, on the premise that the number of subtypes is unknown. It should be noted that the "clusters" in the following descriptions correspond to the "subtypes".

The analyzing process in the hereinafter described CCD method is normally performed on a personal computer on which a dedicated application software program is installed.

Initially, a data set to be analyzed, i.e. mass-spectrum peak information obtained for each of a large number of samples, is obtained (Step S1). Peak information for one sample is obtained by performing a known peak-detection process on the mass spectrum obtained for each sample within a predetermined mass-to-charge ratio range. A piece of peak information is composed of the combination of the mass-to-charge ratio (m/z) value and signal intensity value of a significant peak whose signal intensity value is equal to or higher than a predetermined threshold. In normal cases, a number of significant peaks appear on a mass spectrum. Accordingly, a set of peak information for one sample normally includes a large number of combinations of the m/z value and signal intensity value.

Figure 2:
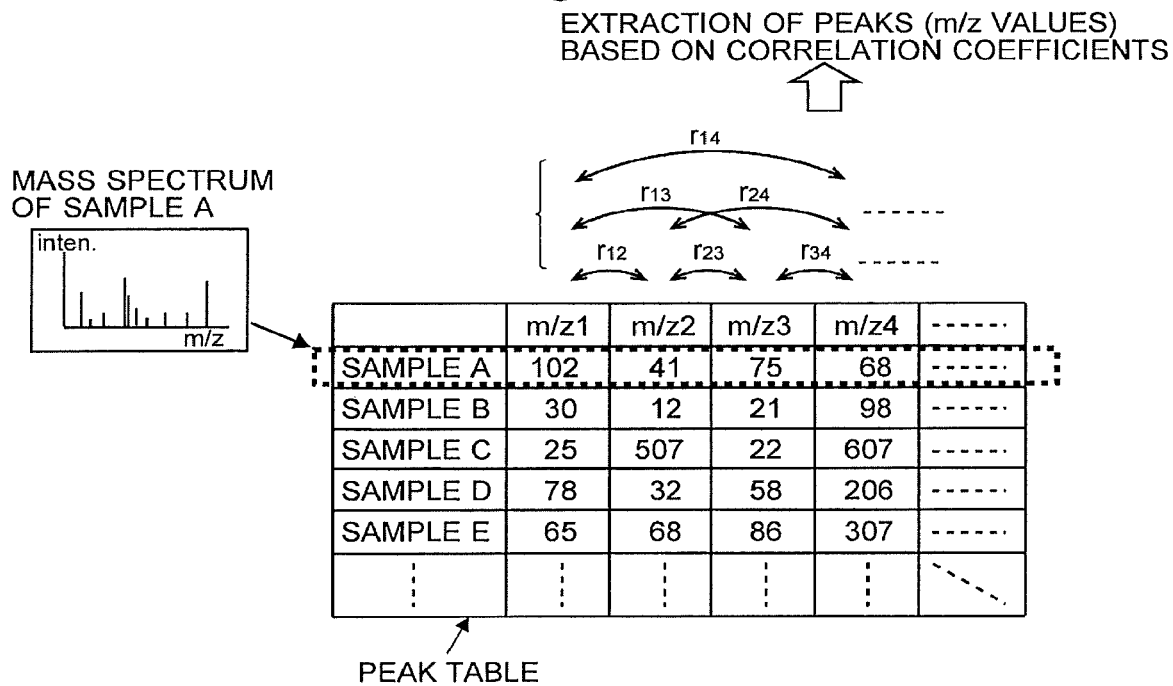
FIG. 2 is a diagram illustrating a peak table as well as a process of calculating the correlation coefficients between the peaks in the big-data analyzing method of the present embodiment.

The peak information collected for each sample in this manner can be compiled into a peak table in a matrix form, e.g. as shown in FIG. 2. In this peak table, each column shows an array of signal intensity values obtained for a number of samples at the same mass-to-charge ratio value (m/z1, m/z2, etc. in FIG. 2). The mass-to-charge ratio values and signal intensity values in the present example correspond to the variable values and quantitative values in the present invention, respectively.

Next, peaks whose signal intensity values are highly correlated with each other are extracted from all samples (Step S2). Specifically, the following process is performed:

Initially, the correlation coefficient $r_{ij}$ of the signal intensity values is calculated for every possible pair of the peaks listed in the peak table (i, j=1 . . . m, where m is the total number of mass-to-charge ratio values, or the total number of cells forming one row of the peak table shown in FIG. 2). For example, as shown in FIG. 2, the correlation coefficients for all possible pairs of the peaks in each sample are exhaustively calculated, i.e. the correlation coefficient $r_{12}$ between the signal intensity values at m/z1 and those at m/z2, correlation coefficient $r_{13}$ between the signal intensity values at m/z1 and those at m/z3, and so on. Subsequently, a plurality of highly correlated peaks are extracted based on their correlation coefficients $r_{ij}$. For example, this can be achieved by extracting each peak having a correlation coefficient $r_{ij}$ equal to or higher than a predetermined threshold, or by extracting each peak which falls within a predetermined proportion (e.g. 10%) of the total number of the peaks among all peaks sorted in descending order of the correlation coefficient.

Figure 3:
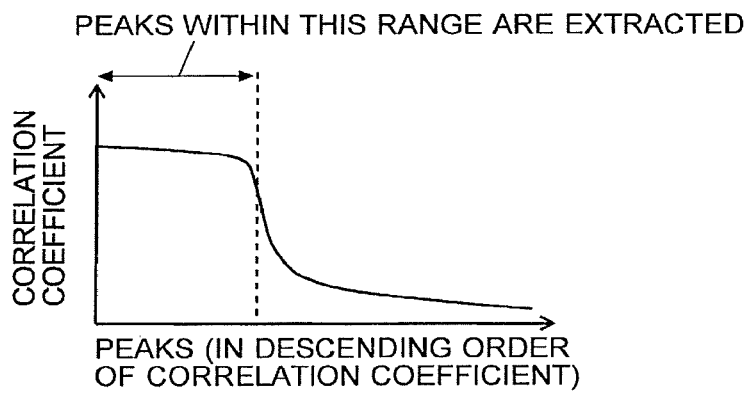
FIG. 3 is a diagram illustrating one example of the method for extracting highly-correlated peaks in the big-data analyzing method of the present embodiment.

If, as shown in FIG. 3, the value of the correlation coefficient considerably decreases at a point on a graph in which the peaks are arranged on the horizontal axis in descending order of the correlation coefficient, the point of change can be considered as a boundary (the broken line in FIG. 3) and the peaks included in a range of correlation coefficients higher than this boundary may be extracted as highly correlated peaks.

The threshold used as a basis for judging the correlation coefficient between the peaks in the previously described manner can be determined as follows: The threshold is gradually decreased from the maximum value of the correlation coefficient value, i.e. 1, in certain steps (e.g. in steps of 0.05), and an analysis using each threshold is performed.

When the threshold is within an appropriate range, the analysis is such conditions as "there are a small number of markers undetected", "almost all markers have been extracted", or "a small number of peaks which are not markers have been additionally extracted". In any of these cases, the analysis result, i.e. the "number of extracted clusters" is the same, and the "selection of markers in each cluster" is also almost the same. The threshold value can be chosen from such a range where the analysis result stabilizes.

It is also possible to use another technique named the "sparse region" method (which will be described later) for automatically determining the threshold used for judging the correlation coefficient between the peaks, and to extract, as highly correlated peaks, each pair of peaks having a higher correlation coefficient than that threshold.

Next, two highly correlated samples having a high degree of similarity of data, or "sample pair", are extracted using the mass-to-charge ratios of a plurality of peaks extracted in the previously described manner (Step S3). Samples belonging to the same cluster are most likely to have a peak at the same mass-to-charge ratio. Therefore, by locating highly correlated peaks, it is possible to find a pair of samples which are likely to eventually belong to the same cluster. Specifically, the following process is performed.

For all possible pairs of the samples, the correlation coefficients rid, (k, L=1 . . . n, where n is the total number of samples) showing the degree of matching of a plurality of mass-to-charge ratios are exhaustively calculated. Subsequently, each sample pair whose correlation coefficient $r_{kL}$ is equal to or higher than a predetermined threshold is extracted. This operation allows one sample to be included in two or more sample pairs. That is to say, if sample A is judged to be highly correlated with both sample B and sample C, both the combination of samples A and B and the combination of samples A and C are extracted as two separate sample pairs. Conversely, a sample which is not significantly correlated with any other sample will not be extracted as a sample pair. In other words, isolated samples which cannot form any pair also naturally exist, and such samples are considered to be unsuitable as cluster candidates and extruded from the cluster determination process. That is to say, at this point in time, samples which are not considered to be useful for cluster formation are excluded from the cluster determination process. Similarly to the case of extracting peak pairs, the threshold to be compared with the correlation coefficient between two samples in order to extract sample pairs can also be automatically determined by the sparse region method (which will be described later).

Figure 4A:
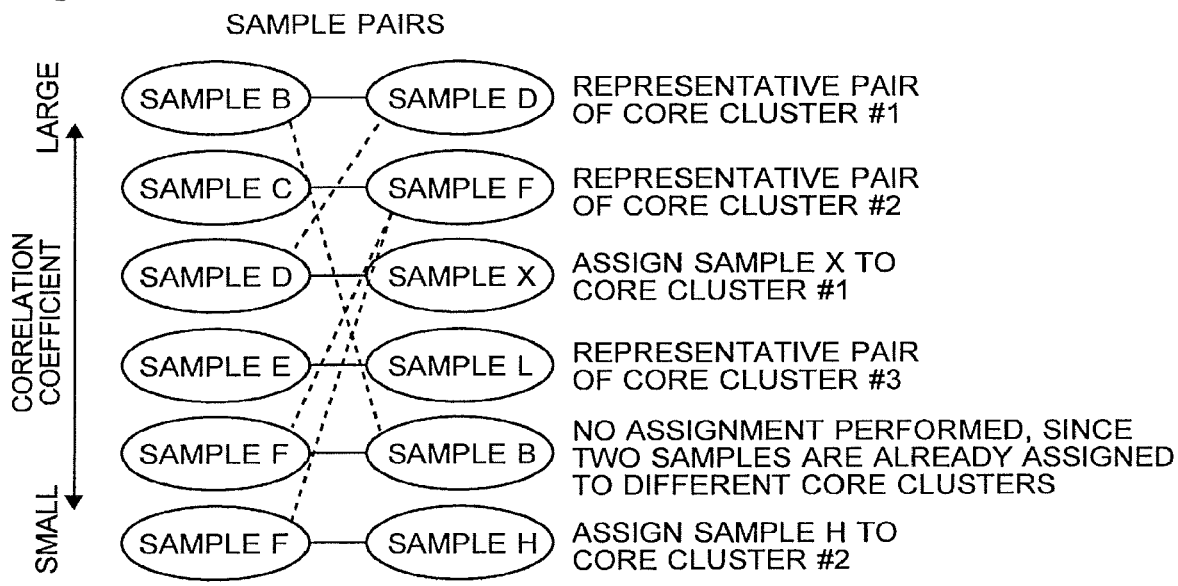
FIGS. 4A and 4B are diagrams illustrating a core cluster formation process in the big-data analyzing method of the present embodiment.
Figure 4B:
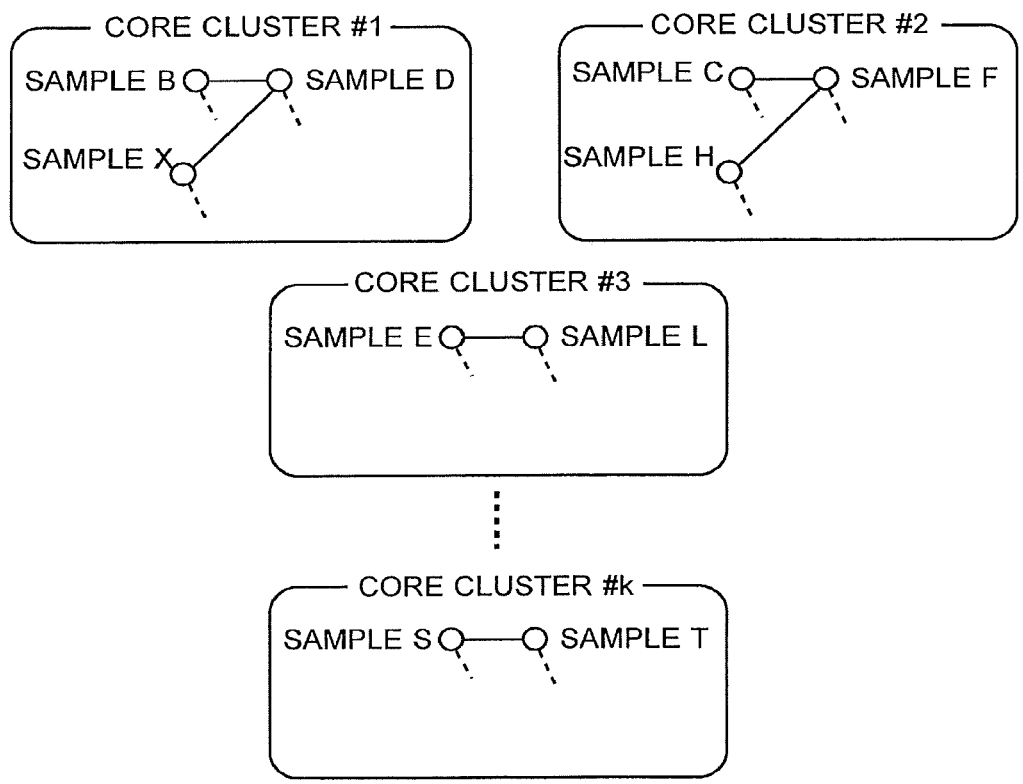

Subsequently, core clusters are formed by successively combining a large number of extracted sample pairs (Step S4). FIGS. 4A and 4B are model diagrams explaining the core cluster formation process.

Initially, the large number of sample pairs extracted in the previously described manner are sorted in descending order of the correlation coefficient $r_{kL}$. In the example of FIG. 4A, the sample pair formed by samples B and D (which is hereinafter written as "sample pair [B, D]") has the highest correlation coefficient, followed by sample pair [C, F], sample pair [D, X] and so on, with their correlation coefficients decreasing from sample pair [B, D] downward.

Next, core clusters are formed by aggregating or combining sample pairs in descending order of the correlation coefficient $r_{kL}$, i.e. with priority given to sample pairs with higher degrees of correlation, according to the following rules.

<Rule 1> A sample pair formed by two samples none of which has yet occurred is designated as the representative pair of a new core cluster (i.e. as the nucleus of a core cluster).

<Rule 2> If only one of the two samples forming a sample pair is included in the samples belonging a core cluster which has already been formed, the other one of the two samples is also assigned to that core cluster.

<Rule 3> A sample pair formed by two samples which respectively belong to two already-formed core clusters is ignored.

In the example of FIG. 4A, sample pairs [B, D] and [C, F] are respectively designated as representative pairs of different core clusters #1 and #2 according to <Rule 1>. In the next (third) sample pair [D, X], sample D has already been a member of core cluster #1. Therefore, according to <Rule 2>, sample X is assigned to core cluster #1. Subsequently, according to <Rule 1>, the fourth sample pair [E, L] is designated as the representative pair of a new core cluster #3. In the fifth sample pair [F, B], the two samples F and B have already been assigned to core clusters #2 and #1, respectively. Therefore, according to <Rule 3>, no process is performed on this sample pair [F, B]. Sample F belonging to the seventh sample pair [F, H] has already been a member of core cluster #2. Therefore, according to <Rule 2>, sample H is assigned to core cluster #2. In this manner, as shown in FIG. 4B, new core clusters are created based on some of the sample pairs extracted in Step S3 while other sample pairs are assigned to existing core clusters.

Needless to say, for such samples that were not extracted as sample pairs in Step S3, i.e. those which were removed from the cluster candidates, the cluster judgment should be deferred. A core cluster which includes only the representative pair (i.e. whose number of samples is two) should preferably be dissolved, with the two samples removed from the cluster candidates.

After all sample pairs extracted in Step S3 have been either compiled into core clusters or left outside the core clusters, one or more singular peaks characterizing a plurality of samples belonging to the core cluster are extracted for each core cluster (Step S5). In the present example, the significant-difference test is used to extract singular peaks.

Specifically, for each core cluster, a commonly known t-test is performed on the difference between the average of the signal intensity values of the peaks at one mass-to-charge ratio in all samples belonging to one target core cluster and the average of the signal intensity values of the peaks at the same mass-to-charge ratio in a group formed by excluding, from all samples, the samples included in the target core cluster. Then, top ten peaks (or any other predetermined number of peaks) are selected in ascending order of the p-value calculated in the t-test (i.e. in order of the probability that the hypothesis is correct), and the selected peaks are designated as the singular peaks in the target core cluster. By this process, ten singular peaks are extracted for each core cluster.

The t-test may be performed on the difference between the average of the signal intensity values of the peaks at one mass-to-charge ratio in all samples belonging to one target core cluster and the average of the signal intensity values of the peaks at the same mass-to-charge ratio in all samples. Although this difference test is slightly less accurate than the previous one, it has the advantage that the calculation time can be shortened.

It should be noted that the singular peaks determined in Step S5 are no more than hypothetical ones. In the next step, those singular peaks are reevaluated and inappropriate singular peaks are removed (Step S6). FIG. 5 illustrates the reevaluation process for singular peaks in specific core clusters. In the present example, each peak which is commonly included in three or more core clusters is judged to be a singular peak, while other peaks are removed from the group of singular peaks.

A set of singular peaks corresponding to a core cluster are characteristic of this core cluster. However, it is unlikely that one singular peak observed in one core cluster cannot be located in any other core cluster, since the analysis is premised on that all samples are basically of the same kind, e.g. all samples have been obtained from the same kind of tissue (e.g. kidney tissue) of different individuals; it is possible to consider that such a peak is probably a noise peak caused by some factors. Accordingly, any peak for which the number of other common peaks (located at the same mass-to-charge ratio) in all core clusters is zero or one, i.e. any peak which is observed in one core cluster but is not observed in any other core cluster or in only one of the other core clusters, is judged as unreliable and removed from the group of singular peaks.

In the example shown in FIG. 5, the peak at m/z=120.1 is located in core cluster #1 but is not present in any other core cluster, i.e. the number of common peaks is zero. Therefore, this peak is removed from the group of singular peaks by reevaluation (the reevaluation result is "NG" in FIG. 5). Similarly, the peak at m/z=123.5 is located in two core clusters #1 and #2 but is not present in any other core cluster, i.e. the number of common peaks is one, so that this peak is also removed from the group of singular peaks by reevaluation. Through this process, each peak which is commonly located in three or more core clusters (the reevaluation result is "OK" in FIG. 5) is maintained in the group of singular peaks. With a denoting the number of peaks removed from a core cluster, if the number of singular peaks extracted in Step S5 is 10, the number of peaks remaining as the singular peaks after the reevaluation is $10-\alpha$. The value of $\alpha$ is different for each core cluster.

Subsequently, a cluster in which a plurality of core clusters are integrated is created using the singular peaks which have been extracted and reevaluated for each core cluster in the previously described manner (Step S7).

Specifically, the entire group of core clusters is searched for to locate a combination of two or more core clusters which have three or more singular peaks commonly included in the $10-\alpha$ singular peaks extracted for each core cluster, i.e. which have three or more common mass-to-charge ratios at which peaks are located. For the core clusters located by this search, a flag which indicates that those core clusters have a strong probability for integration (this flag is hereinafter simply called the "flag") is added.

FIG. 6 illustrates the process for investigating the integratability of the core clusters. In the example shown in FIG. 6, three core clusters #1, #2 and #3 share three common peaks p1, p2 and p3. Accordingly, a flag is added to these three core clusters #1, #2 and #3. Two core clusters #4 and #5 share three common peaks p4, p5 and p6. Accordingly, a flag, which is different from the first one, is added to these two core clusters #4 and #5. By comparison, core cluster #6, which has only two common peaks p4 and p5 shared with core clusters #4 and #5, does not satisfy the aforementioned condition. Accordingly, no flag is added.

Subsequently, the following judgment process is performed on the core clusters to which the flags have been added.

Consider the case where there are two core clusters which are considered to have a strong probability for integration. One of the two core clusters including a sample pair having a relatively higher value of the correlation coefficient $r_{kL}$ is denoted by $\alpha$, and the other core cluster by $\beta$. Whether or not two thirds (or one half, or any other predetermined proportion) of all singular peaks of core cluster $\alpha$ are possessed by core cluster $\beta$ is determined. Similarly, whether or not two thirds (or one half, or any other predetermined proportion) of all singular peaks of core cluster $\beta$ are possessed by core cluster $\alpha$ is also determined. If both conditions are satisfied, the two core clusters are integrated into one cluster. If there are two or more core clusters satisfying the aforementioned conditions, those core clusters are similarly integrated to expand the cluster. An isolated core cluster, i.e. a core cluster which cannot be integrated with any other core cluster, should not be adopted as a core cluster, and the samples belonging to this core cluster should be removed from cluster candidates.

Figure 7:
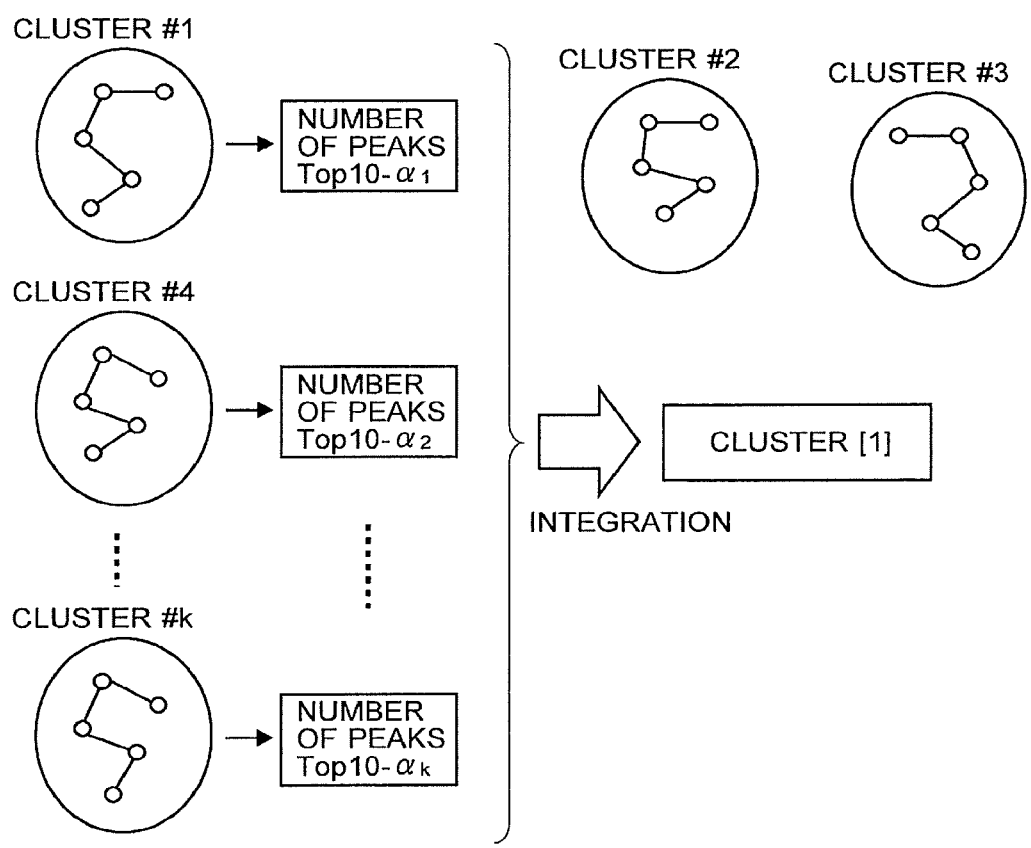
FIG. 7 is a diagram illustrating a process of forming clusters by cluster integration in the big-data analyzing method of the present embodiment.

In this manner, the integration process is attempted for all core clusters formed in Step S4, whereby a plurality of clusters are created (needless to say, in principle, it is possible to have all core clusters aggregated into one cluster). FIG. 7 illustrates the process of forming clusters by cluster integration. In this example, three clusters #1, #4 and #k are integrated into one cluster. In the following description, a cluster created by integration is written as "cluster [*]", with "*" denoting the cluster number.

Next, singular peaks are extracted for each of the determined clusters (Step S8). For example, each cluster includes a plurality of core clusters, with each core cluster having $10-\alpha$ singular peaks, as described earlier. Accordingly, for each cluster, each singular peak located at a mass-to-charge ratio which is shared by one half or more of the core clusters included in the cluster concerned can be extracted as a singular peak for the same cluster.

It is also possible to extract singular peaks for each cluster as follows:

For each cluster, the average of a characteristic value of the peaks in the cluster and the average of the same characteristic value of the peaks in the other clusters are calculated, and a commonly known t-test is performed on the difference between the two averages. The peaks are sorted in ascending order of the p-value calculated in the t-test, and the peaks having sufficiently small p-values are chosen as singular peaks. If the cluster to be tested is a simple-type cluster, the control cluster to be compared should be refined by excluding, from the control group of the t-test, the members of a mixed cluster in which the cluster being tested is included as a mixture. If the cluster to be tested is a mixed cluster, the members of each single cluster included in the mixed cluster as a mixture should be excluded from the control group. Whether or not a peak has a sufficiently small p-value can be determined by detecting a phase in which the rate of change in the p-value rapidly changes. Accordingly, based on the calculated p-values, $Y=-\log 10(\text{p-value})$ is computed for each p-value. Examining about 30 peaks having small p-values is sufficient for practical purposes since singular peaks of real clusters are most likely be included in those 30 peaks. Accordingly, a moving average of three successive Y values is calculated in order of the sorted peaks. After the calculation is started from peak ranked $30^{th}$ toward the higher-ranked peaks with smaller p-values, when a peak at which the moving average differs from the previously calculated value by greater than two is detected, the peaks having smaller p-values than the detected peak are extracted as the singular peaks.

After that, for each cluster, a member determination formula for determining whether or not a sample belongs to the cluster by using a plurality of singular peaks of the cluster is created (Step S9). In the present example, a logistic regression model (which will be hereinafter described) is used to construct the member determination formula. Before the model construction, whether or not three or more of the singular peaks of one cluster are also included in the singular peaks of another cluster is determined. Any cluster having three or more such peaks is considered to be a mixed core cluster, and samples included in such a cluster are removed from the set of samples to be used for the construction of the logistic regression model. Such a preprocessing is necessary because, if such samples are not removed, samples belonging to the same cluster will be mixed in the two groups subjected to the two-group judgment and lower the accuracy of the logistic regression model.

<Logistic Regression Model>

In the present case,

Y=1 means that the sample (member) concerned belongs to the target cluster, and

Y=0 means that the sample (member) concerned belongs to a cluster different from the target cluster.

With $Pr(Y=1|X)$ representing the probability that a given singular-peak group X of a cluster yields the result of Y=1, the logistic regression model is given by the following equation:

$$Pr(Y=1|X)=1/[1+\exp\{-(b_0+b_1X_1+b_2X_2+\ldots+b_kX_k)\}]$$

where $X_k$ is a variable value of the $k^{th}$ singular peak X, which takes a value of the peak intensity as a characteristic value of each patient, while $b_0, b_1, \ldots, b_k$ (k=1, ..., K) are parameters estimated from highly reliable data, with K representing the number of singular peaks of the cluster concerned.

Substituting the characteristic values of the singular peaks observed for a patient into the aforementioned logistic regression formula yields a probability value which can be used for determining whether or not the patient belongs to the cluster concerned. An example of the determination rule is that the patient should be classified into a cluster having the highest probability value which has been calculated for each cluster. As another example, the patient may be classified into each cluster having a probability value of ½ or higher. According to this determination rule, the same patient is allowed to belong to two or more clusters. The probability-based determination can be used to reevaluate the reliability of the samples for which highly reliable data have been obtained, while removing low-probability samples from the cluster into a low-reliability data set for a later and final judgment. This determination can also be applied to all samples in the low-reliability data set to assign each sample to an appropriate cluster.

The member determination formula constructed in the previously described manner yields the result of Y=1 for a sample which unmistakably belongs to a specific cluster or Y=0 for a sample which cannot belong to that specific cluster (i.e. which unmistakably belongs to a different cluster). The closer to 1 the value of Y is, the more likely the sample belongs to that specific cluster.

Next, in order to verify the member determination formula corresponding to each cluster, the data on each sample included in the cluster are substituted into the member determination formula to calculate the determination result for that sample. If the calculated probability is low, the sample will not be classified into the cluster by the member determination formula. Accordingly, if the determination result (Y value) is not higher than 0.5, the sample is removed from the cluster (Step S10).

Removing some of the samples from the cluster may possibly change the selection of the singular peaks. Accordingly, the selection of the singular peaks are revised based on the data on the samples remaining in the cluster (Step S11). Even a single change of the selection of the singular peaks leads to a change in the member determination formula. Accordingly, as in Step S9, the member determination formula is reconstructed based on the modified selection of the singular peaks (Step S12). By this process, the accuracy of the member determination formula can be improved. The process from Step S8 through S12 may be repeated a plurality of times. However, in practice, a single revision of the selection of the singular peaks, followed by the reconstruction of the member determination formula, can yield a sufficiently reliable determination formula, as shown in the flowchart of FIG. 1.

As a result, the following items of information are fixed: clusters (i.e. subtypes); singular peaks selected for each cluster (i.e. biomarkers characterizing each subtype); and member determination formulae for determining which cluster a sample belongs to. The fixed clusters may possibly include a cluster which is a mixture of a plurality of other clusters (such a cluster is hereinafter called the "mixed cluster"). Accordingly, for each cluster, whether or not the singular peaks of one cluster overlap the singular peaks of two or more other clusters is determined. Based on the result, whether or not the cluster concerned is a mixed cluster is determined, and furthermore, if the cluster is a mixed cluster, the clusters mixed in it are identified (Step S13).

Subsequently, for each of all samples given as the target to be analyzed (including those which have already been sorted into clusters), the sample's probabilities of the assignment to the clusters (including mixed clusters) are calculated using the member determination formulae corresponding to those clusters. Based on the calculated result, a cluster which the sample belongs to is determined (Step S14), and the result is provided as output information (Step S15).

Specifically, for each sample, if one of the probabilities of the assignment to a plurality of clusters is equal to or greater than a predetermined threshold, it is possible to conclude that the sample belongs to the cluster giving that probability. If there are two or more clusters with the assignment probabilities equal to or greater than the threshold, it is possible to conclude that the sample belongs to those clusters. If none of the probabilities of the assignment to the plurality of clusters is equal to or greater than the threshold, it is possible to conclude that the assignment is indeterminable due to some reasons; e.g. the sample may be an erroneously mixed sample which is not actually a target of the analysis, or the technique, conditions or other factors concerning the measurement for the sample are incorrect. Alternatively, the sample may automatically be assigned to a cluster which gives the highest assignment probability, without setting the threshold for judging the assignment probability. In this case, a single cluster which the sample belongs to can be determined.

Figure 8:
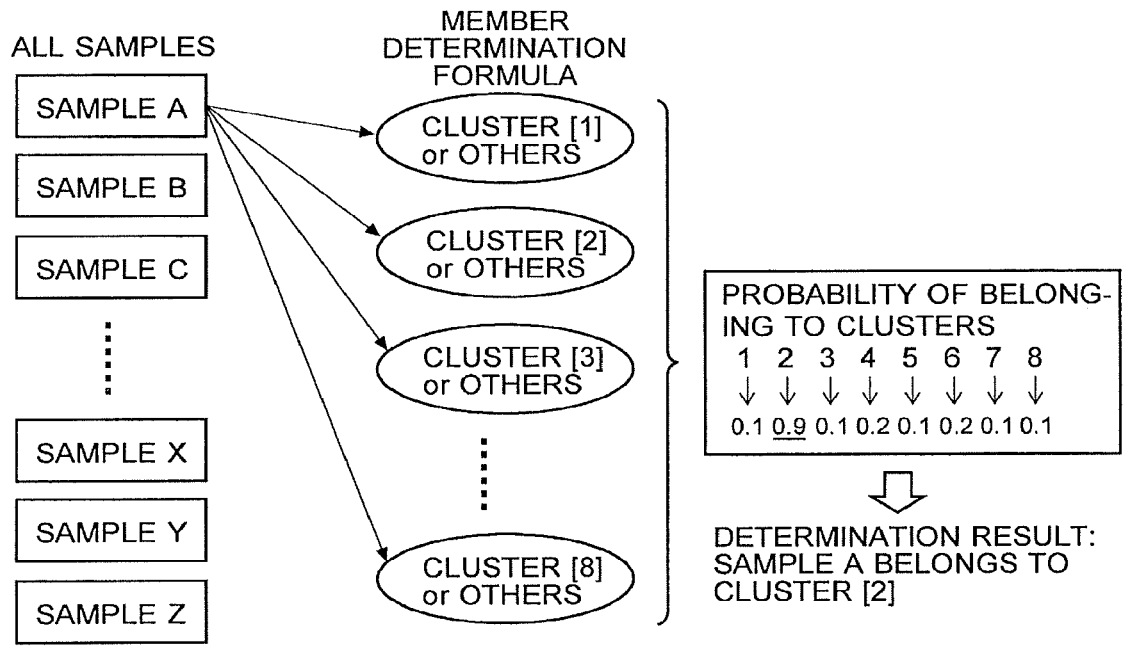
FIG. 8 is a diagram illustrating a process for determining the assignment of samples to clusters in the big-data analyzing method of the present embodiment.

FIG. 8 is a model diagram showing the judgment process for each sample. In this example, there are a total of eight clusters. Consider the situation where the data of sample A have been substituted into the eight member determination formulae corresponding to those clusters, with the result that the assignment probabilities to those clusters have been obtained as shown in the right area of FIG. 8. The probability for cluster [2] has the highest value of 0.9, whereas the probabilities for all other clusters are as low as 0.2 or less. Accordingly, sample A is judged to be a member of cluster [2]. As noted earlier, a cluster may be a mixed cluster. If a sample is judged to be a member of a mixed cluster, it is possible to conclude that the sample concerned belongs to both clusters from which the mixed cluster is formed.

As described thus far, by the CCD method, a plurality of subtypes of a cancer as well as biomarkers (mass-to-charge ratio values) for identifying those subtypes can be determined based on mass spectrum data obtained by performing a mass spectrometric analysis on samples obtained from a number of patients suffering from a cancer at the same site or in the same biological tissue or internal organ. A member determination formula for determining the subtype which a sample belongs to can also be created. By using the member determination formulae, one or more subtypes to which a sample belongs to can be determined.

[Description of Sparse Region Method]

Hereinafter described in detail is the sparse region method which can be used to automatically determine the threshold for judging the correlation coefficient in Steps S2 and S3.

Figure 13:
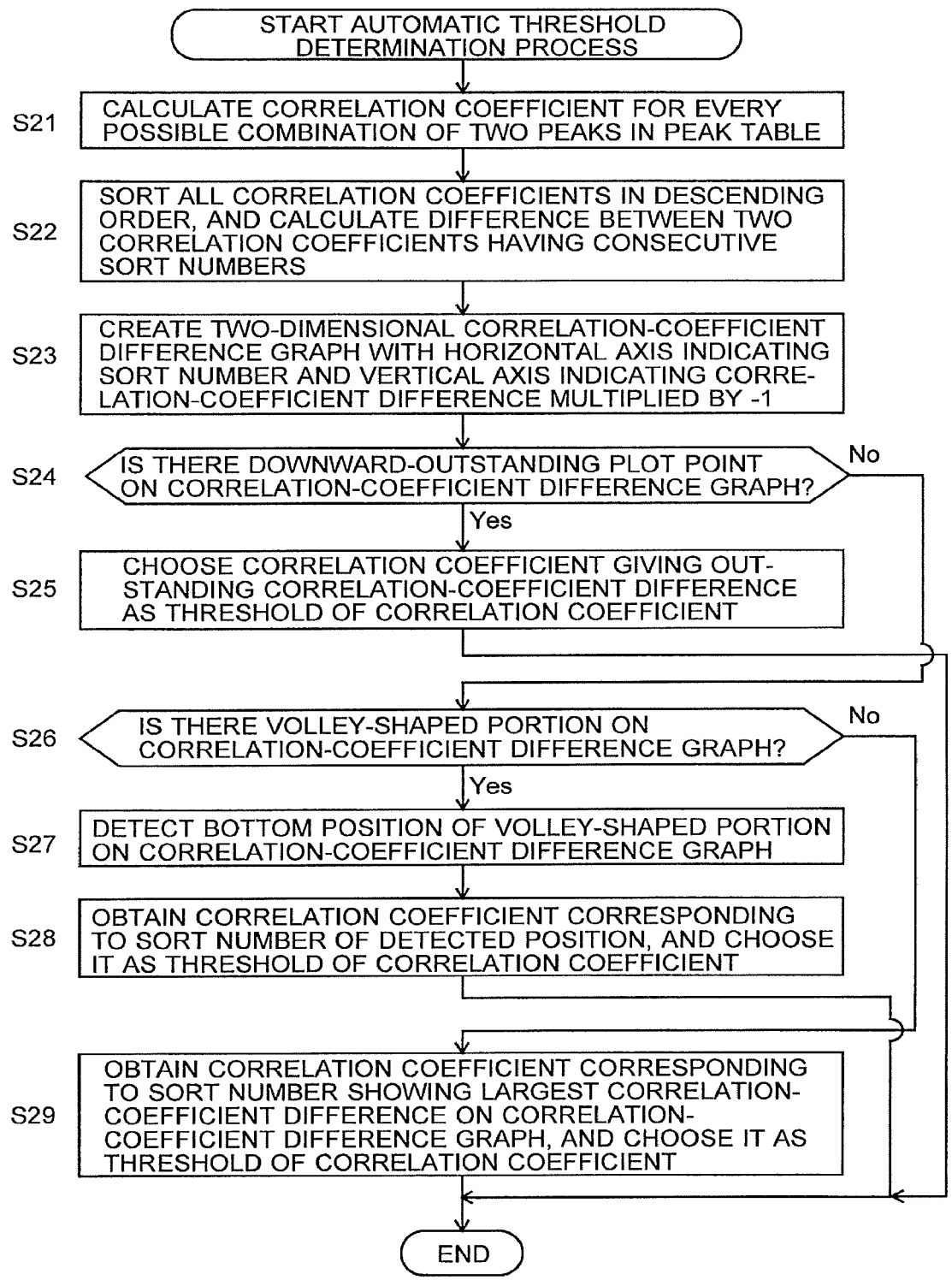
FIG. 13 is a flowchart of a process for automatically determining the threshold for judging the correlation coefficient by the sparse region method in the big-data analyzing method of the present embodiment.

FIG. 13 is a flowchart showing a process for automatically determining the threshold for judging the correlation coefficient by the sparse region method. FIGS. 14-18 are graphs for explaining the same process for automatically determining the threshold for judging the correlation coefficient. The following description deals with the case of determining the threshold for judging the correlation coefficient between the peaks in Step S2. It is evident that the threshold for judging the correlation coefficient between samples can also be determined in a similar manner.

At the beginning of the threshold determination process, the correlation coefficient $r_{ij}$ of the signal intensity values is calculated for every possible pair of the peaks listed in a peak table as shown in FIG. 2 (Step S21). Next, all correlation coefficients $r_{ij}$ are sorted in descending order of the calculated value, labeled with sort numbers, and the difference between each pair of the correlation coefficients having consecutive sort numbers is calculated (Step S22). Needless to say, the correlation coefficients $r_{ij}$ may be sorted in ascending order of the calculated value instead of the descending order. Based on the calculated result of the correlation-coefficient difference, a graph of the correlation-coefficient difference is created, with the horizontal axis indicating the sort number and the vertical axis indicating the value obtained by multiplying by −1 the difference between the correlation coefficients having consecutive sort numbers (Step S23). Needless to say, this graph does not need to be directly presented to users (analysis operators); it is a virtual graph created for convenience of the computation. The operation of multiplying the correlation-coefficient difference by −1 is intended to convert correlation-coefficient differences into negative values so that the graph which will be described later becomes easier to view. Such a conversion into negative values is not always necessary.

Figure 14:
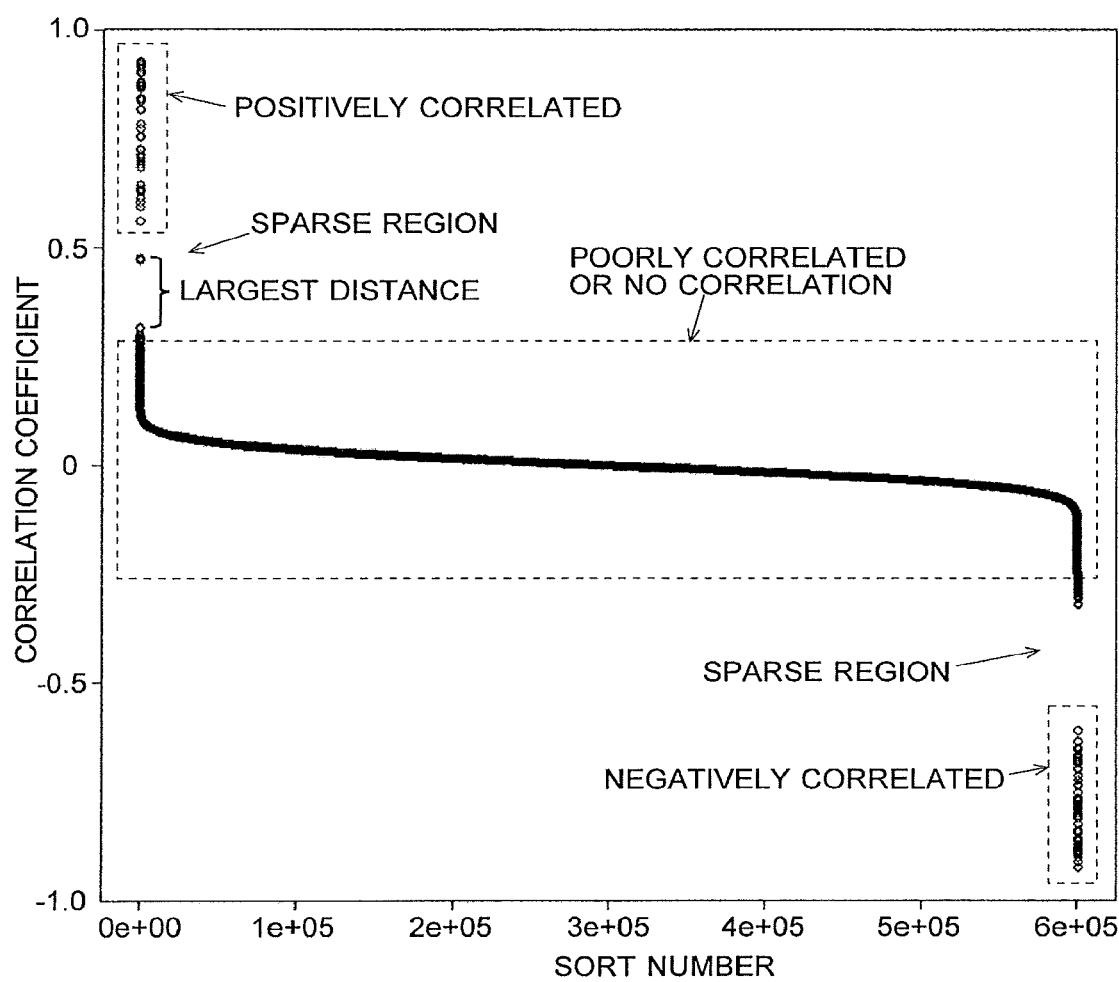
FIG. 14 is a chart illustrating the process for automatically determining the threshold for judging the correlation coefficient shown in FIG. 13.

FIG. 14 is a graph showing the correlation coefficients between the peaks calculated from simulation data created by processing actually measured mass spectrum data (which will be described later), with the correlation coefficients arranged in order of the sort number. The total number of peaks is 1097, and that of the correlation coefficients between the peaks is $_{1097}C_2=601,156$. Normally, the correlation coefficient between any two peaks belonging to the same subtype should have a larger absolute value (closer to one), while the correlation coefficient between any two peaks which do not belong to the same subtype should have a smaller absolute value (closer to zero). Therefore, when the correlation coefficients are arranged in descending order, two groups of data points are formed, as shown in FIG. 14, including a group of data points having larger absolute values of the correlation coefficient, i.e. a group of data points having a significant degree of positive or negative correlation, and another group of data points having smaller absolute values of the correlation coefficient, i.e. a group of data points having a low degree of positive or negative correlation or practically no correlation. Between these two groups, a "sparse region", i.e. a region in which the data points are sparsely located, is formed. In the sparse region method, a reasonable threshold which is suitable for judging the correlation coefficient is determined by detecting the sparse region.

FIGS. 15-18 are correlation-coefficient difference graphs created on the basis of the correlation coefficients shown in FIG. 14. In any of these graphs, the horizontal axis indicates the sort number of the correlation coefficient and the vertical axis indicates the difference in the two neighboring correlation coefficients after the sorting. FIG. 15 shows the correlation-coefficient difference for almost all pairs of the peaks, whereas FIGS. 16, 17 and 18 show the correlation-coefficient difference between the peaks with the sort numbers limited to 1-10000, 1-1000 and 1-100, respectively.

As can be seen in FIG. 14, the group of data points having larger absolute values of the correlation coefficient has a comparatively high plot density of the data points. Similarly, the group of data points having smaller absolute values of the correlation coefficient also has a comparatively high plot density of the data points. By comparison, the plot density of the data points in the region between the two groups is low. Therefore, in the correlation-coefficient difference graph, the data-point distribution has a volley-shaped portion (i.e. downward-convex form) around the sort number at which the difference between the correlation coefficients with consecutive sort numbers becomes the largest value. In each of FIGS. 15-18, the data point located at the bottom of the correlation-coefficient difference distribution forming the volley-shaped portion is indicated by the thick arrow. In particular, in the present example, as shown in FIG. 14, there is a location at which the difference between the correlation coefficients having consecutive sort numbers extremely increases, so that the correlation-coefficient difference at the deepest point of the volley-shaped portion is solely outstanding in the downward direction. Therefore, by using, as the threshold, the correlation coefficient having the sort number corresponding to the deepest point of the volley-shaped portion, it is possible to determine, with a high degree of reliability, that the correlation of the peaks within a range of correlation coefficients higher than the threshold is high, whereas the correlation of the peaks is low or there is practically no correlation within a range of correlation coefficients lower than the threshold. The same also hold true for the case where the correlation coefficients are not converted into negative values, except that a peak-shaped portion (i.e. upward-convex form) is formed instead of the valley-shaped portion.

Accordingly, after the correlation-coefficient difference graph has been obtained, whether or not there is a single downward-outstanding plot point of the correlation-coefficient difference in the distribution of the correlation-coefficient difference is determined (Step S24). Whether or not a plot point is outstanding can be determined, for example, based on a change in the value of the correlation-coefficient difference. If it is determined that there is a single outstanding plot point, the correlation coefficient giving the correlation-coefficient difference of the plot point is chosen as the threshold (Step S25).

On the other hand, if it is determined that there is not a single downward-outstanding plot point of the correlation-coefficient difference, whether or not there is a downward-convex portion (i.e. valley-shaped portion) in the distribution of the correlation-coefficient difference is determined (Step S26). If the downward-convex portion is present, the deepest point of the valley portion is located (Step S27), and the correlation coefficient corresponding to the sort number at the located point is determined. If there are two or more valley-shaped portions, the valley-shaped portion with the smallest sort number (in the case of the descending sort) can be selected. If there is a single valley-shaped portion whose bottom is spread at approximately the same depth or there are two or more bottom portions at approximately the same depth, the smallest sort number within the bottom portion (or portions) can be located. The correlation-coefficient value determined in this manner is chosen as the threshold (Step S28).

In some cases, no clear valley-shaped portion may be formed in the distribution of the correlation-coefficient difference on the correlation-coefficient difference graph. Accordingly, if the determination results in both of Steps S24 and S26 are "No", the correlation coefficient corresponding to the sort number giving the largest correlation-coefficient difference on the correlation-coefficient difference graph is determined, and its value is chosen as the threshold (Step S29). If there are two or more sort numbers giving the largest correlation-coefficient difference on the correlation-coefficient difference graph, the smallest sort number can be chosen.

In this manner, an appropriate threshold for judging the correlation coefficient between the peaks can be automatically determined.

The process from Steps S24 through S28 may be replaced by a process in which a function which appropriately fits to the data points is defined as the fitting function, and the correlation coefficient corresponding to a local minimum of this function is chosen as the threshold. It is also possible to choose, as the threshold, not the correlation coefficient corresponding to the bottom point in the valley-shaped portion, but the correlation coefficient at a point intentionally displaced from the bottom point toward smaller sort numbers, or conversely, toward larger sort numbers. For example, if it is preferable to avoid a mixture of inappropriate peaks while allowing for an omission of a small number of appropriate peaks, a correlation coefficient corresponding to a point displaced toward smaller sort numbers may be chosen as the threshold so as to set the threshold at a slightly higher level. Conversely, if it is preferable to minimize the omission of appropriate peaks while allowing for a mixture of a small amount of inappropriate peaks, a correlation coefficient corresponding to a point displaced toward larger sort numbers may be chosen as the threshold so as to set the threshold at a slightly lower level.

Instead of automatically determining the threshold in the previously described manner, the system may be configured so that the correlation-coefficient difference graph is displayed on the screen of a display unit, and when an analysis operator performs a click operation using a pointing device (e.g. mouse) at an appropriate position on the graph, a correlation coefficient corresponding to the closest position to the point at which the click operation has been performed is set as the threshold. In this case, the threshold is not automatically determined, but a piece of information for determining the threshold is presented to users, allowing the users manually set the threshold. The system may also be configured so that an automatically determined threshold can be appropriately modified on the correlation-coefficient difference graph.

In the case where the distribution of the data points on the correlation-coefficient difference graph shows neither the downward-outstanding correlation-coefficient difference nor forms a clear volley-shaped distribution, there are some possible situations; e.g. the difference in signal intensity between the group of singular peaks in the cluster and the group of non-singular peaks is insufficient, or the number of singular peaks is too small. In such a situation, the subtype classifications as well as the markers characterizing each subtype obtained as a result of the analysis by the CCD method may be unreliable. Accordingly, the system may be configured to inform users of the situation if the determination results in both of Steps S24 and S26 are "No", thus allowing the users to make judgment on whether or not the data being analyzed are unanalyzable by the CCD method.

[Example of Analysis by CCD Method]

In order to confirm the usefulness of the CCD method, the present inventors have conducted an analysis of simulation data created by processing actually measured mass spectrum data, and evaluated the result of the analysis.

To prepare the simulation data, mass spectrum data were obtained by performing a measurement on a sample containing a mixture of five kinds of protein digests (peptides) using a liquid chromatograph-matrix assisted laser desorption ionization/time-of-flight mass spectrometer (LC-MALDT/TOFMS), and the signal intensity of each peak on the mass spectrum was randomly changed to obtain a number of virtual mass spectra (i.e. a number of samples). These data were intended to simulate peak information of mass spectra for cancerous tissues sampled from a number of patients suffering from a type of cancer which could be classified into a plurality of simple subtypes as well as a plurality of mixed subtypes in which two simple subtypes were mixed together. The mass-to-charge ratios of the peaks on the mass spectrum were within a range of 800-2000. The total number of the peaks was 1097.

The peak creation conditions were as shown in FIG. 10: The number of subtypes was eight, including five simple subtypes, two mixed subtypes each of which contains two simple subtypes mixed together, and one subtype for healthy individuals who have no cancer. In this case, the subtypes substantially correspond to the aforementioned clusters. Accordingly, in the following description, the subtype number is denoted by [*], with the five simple subtypes labeled [1]-[5], two mixed subtypes labeled [6] (=[1]+[3]) and [7] (=[2]+[4]), and the subtype for normal individuals labeled [8]. The number of samples per subtype was 100; i.e. the total number of samples was 800. The number of singular peaks (which correspond to biomarkers) chosen for each subtype was 10.

FIG. 11 shows a list of m/z values of the singular peaks for each subtype. Each m/z value underlined in FIG. 11 corresponds to a peak at which the signal intensity (or specifically, the amount of component corresponding to the peak) in a cancerous case is higher than in the case of healthy individuals regardless of the subtype. In other words, this peak is a common marker shared by a plurality of subtypes. Singular peaks in the other subtypes are indicated by the upward or downward arrow on the right side of the m/z values. Specifically, the upward arrow (↑) indicates that any sample belonging to this subtype has a higher signal intensity of the peak at this m/z value than the samples belonging to the other subtypes. Similarly, the downward arrow (↓) indicates that any sample belonging to this subtype has a lower signal intensity of the peak at this m/z value than the samples belonging to the other subtypes. It should be noted that the simulation data used in this example were intentionally adjusted so that a certain amount of difference in the signal intensities of the specific peaks occurs among the subtypes. Specifically, in the present example, a singular increase in the intensity of a peak was simulated by doubling the corresponding intensity for healthy individuals, while a singular decrease was simulated by halving the corresponding intensity.

The previously described CCD method was applied to the aforementioned simulation data prepared for 800 samples. Initially, as the process in Step S2, for each sample, the correlation coefficient was calculated for every possible pair of the 1097 peaks, i.e. for each of $_{1097}C_2=601,156$ pairs of the peaks. The calculated result was judged by the method shown in FIG. 3, and peaks were extracted. The condition for the extraction was that the correlation coefficient should be equal to or lower than −0.5 or equal to or higher than 0.5. As a result, 96 peaks were extracted.

Next, as the processes in Steps S3 and S4, the correlation coefficient was calculated for every possible pair of 800 samples, i.e. for each of $_{800}C_2=31,960$ sample pairs. Sample pairs having correlation coefficients 0.9 or higher were extracted and combined. As a result, 53 core clusters were created. By sequentially performing the previously described processes in this manner, the number of clusters was eventually decreased to eight. This number is equal to the subtype number specified in the creation conditions, and therefore, the correct result. FIG. 12 shows what subtype each cluster belongs to, determined by comparing the eventually fixed singular peaks in the cluster with the peaks shown in FIG. 11.

As can be understood from in FIG. 12, for subtypes [1]-[5] which are all simple subtypes, all markers except m/z=1073.6, 1123.7 and 1405.8 are extracted as singular peaks. These three singular peaks which have not been extracted are duplicate markers included in two or more subtypes. These are previously chosen peaks whose signal intensities in a sample having any of the subtypes (i.e. any specimen having the cancer) always become higher than in a sample obtained from a healthy individual. Accordingly, those peaks have no substantial difference in the signal intensity among the subtypes, and therefore, cannot be considered as characterizing peaks for a subtype. Furthermore, these three singular peaks are extracted as markers for subtype [8] prepared for healthy individuals. Therefore, the fact that the three peaks have not been extracted as markers for subtypes [1]-[5] is a reasonable result.

In the present example, if the singular peaks of one subtype include three or more singular peaks of a different subtype, and if there are two or more kinds of such different subtypes, the subtype is judged to be a mixed subtype. In FIGS. 11 and 12, the number written in the brackets placed after the m/z value of each singular peak in subtypes [6] and [7] is the subtype number of a different subtype which has the singular peak concerned. The result shows that subtypes [6] has three or more singular peaks of each of subtypes [1] and [3], which means that subtype [6] is a mixed subtype of subtypes [1] and [3]. Similarly, subtype [7] is a mixed subtype of subtypes [2] and [4]. Both results are correct answers. Thus, it has been confirmed that both simple subtypes and mixed subtypes have been correctly classified. Additionally, it was also checked whether or not each sample sorted into one of the eight subtypes by the CCD method was a correct sample which should actually belong to that subtype. The percentage of the correct answers was 100%. Thus, it was confirmed that all of the 800 samples were correctly classified.

Similar tests were also conducted under stricter analytical conditions, such as a smaller difference in the intensities of the singular peaks (markers) between healthy individuals and cancer patients, or the number of singular peaks being less than 10 (although at least two), or the number of samples being less than 100 for each subtype. Those tests confirmed that 90% or higher percentages of the sample could be correctly classified by setting an appropriate threshold in each step. Accordingly, it is possible to conclude that the classification into subtypes (clusters) by the CCD method can be performed with a high degree of reliability.

[Mass Spectrometric System Using CCD Method]

The configuration and operation of one embodiment of the mass spectrometric system using a data analysis by the previously described big-data analyzing method of the present embodiment is hereinafter described.

Figure 9:
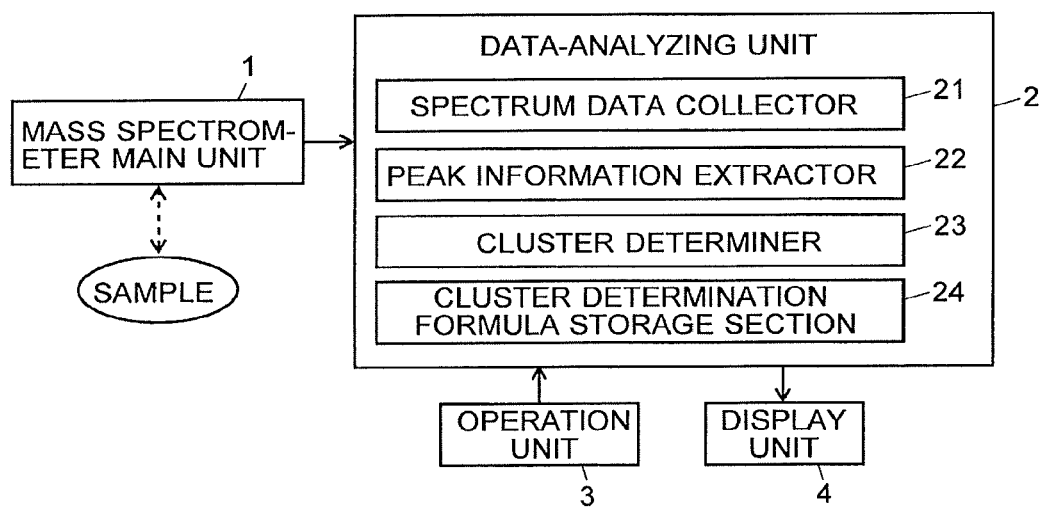
FIG. 9 is a schematic configuration diagram of a mass spectrometric system using the big-data analyzing method of the present embodiment.

FIG. 9 is a block configuration diagram showing the main components of the present mass spectrometric system.

The mass spectrometric system of the present embodiment includes a mass spectrometer main unit 1, data analyzing unit 2, operation unit 3 and display unit 4. An example of the mass spectrometer main unit 1 is a time-of-flight mass spectrometer provided with a MALDI (matrix-assisted laser desorption ionization) ion source, which is capable of acquiring high-accuracy and high-sensitivity mass spectrum data for a set sample over a predetermined range of mass-to-charge ratios. The data analyzing unit 2 is actually a personal computer on which a dedicated data-analyzing software program or similar application is previously installed. By executing this software program on the personal computer, various functional blocks are embodied, such as a spectrum data collector 21, peak information extractor 22, cluster determiner 23, and cluster determination formula storage section 24. The operation unit 3 is a keyboard and pointing device, which are normally included in (or connected to) the personal computer. The display unit 4 is a monitor.

Normally, at least the processes from Steps S1 through S11 in the CCD method are performed by a comparatively high-performance computer, and the member determination formula thereby obtained for each cluster is stored in the cluster determination formula storage section 24. In other words, in the present example, the data analyzing unit 2 does not have the function of performing the processes from Steps S1 through S11. Since there is one member determination formula for each subtype and each site of cancer, it is preferable to prepare one set of member determination formulae for each site of cancer (e.g. breast cancer, kidney cancer, etc.) and store them in the cluster determination formula storage section 24 so that an appropriate set of member determination formulae for a site of cancer to be identified can be read from the cluster determination formula storage section 24 into the cluster determiner 23 when the site of cancer is specified by an operator using the operation unit 3.

After one sample is set in the mass spectrometer main unit 1, the mass spectrometer main unit 1 performs a mass spectrometric analysis on that sample. The spectrum data collector 21 collects mass spectrum data obtained by the analysis and holds the data in a memory. The peak information extractor 22 performs a peak detection process on the stored mass spectrum data and collects the mass-to-charge ratio values and signal-intensity values of the peaks observed on the mass spectrum as peak information. The cluster determiner 23 determines a subtype which the sample may possibly belong to, based on one set of member determination formulae read from the cluster determination formula storage section 24 into the cluster determiner 23. This process is effectively the same as the process performed in Step S14. The determination result is displayed on the screen of the display unit 4 to inform a test operator or similar individual of the result.

In this manner, with the mass spectrometric system of the present embodiment, it is possible to conveniently determine the subtype of a cancer based on a sample taken from a patient suffering from the cancer. The determination result can be provided in various output forms. For example, after one or more subtypes are identified by judging the assignment probabilities calculated by different member determination formulae according to a previously defined rule, the identified subtypes may be solely displayed. The values of the assignment probabilities may also be displayed along with the identified subtypes. The assignment probabilities for all subtypes may also be displayed.

The assignment probabilities may also be displayed in a graphical form instead of the numerical form, whereby the assignment probabilities for different subtypes can be visually and easily compared. Furthermore, if a cure method or the like is to some extent established for each subtype, the cure methods or the like corresponding to the subtypes can also be displayed in relation to the subtypes.

As already noted, if the calculated result shows an unmistakably low assignment probability for any subtype, there are some possible reasons; e.g. the sample itself was inappropriate, the analysis was incorrectly performed, or the site of cancer was incorrectly specified. In such situations, the system should preferably display an alert message.

The previous embodiment is concerned with the case where the big-data analyzing method according to the present invention is used for determining the subtype of a cancer. The big-data analyzing method according to the present invention is not limited to this case but can also be applied to various measurement targets or data analysis in various areas.

The type of data which can be treated by the big-data analyzing method according to the present invention are a number of sets of data respectively obtained for a large number of samples, with each set of data including a quantitative value (e.g. observation values, measurement values, or instrumentation values) with respect to a predetermined variable. In the previously described example, the variable value is the mass-to-charge ratio value, while the quantitative value is the signal intensity value.

Another application example is the next-generation sequencer analysis for examining the base sequence of the entire DNA in a cell, in which case the variable value is the position information on the genome while the quantitative value is the read number of a mutated base among the four bases. In the case of the microarray analysis (transcriptome analysis) for examining all transcripts (mRNA) in a cell, the variable value is the name of the gene probe set on the microarray while the quantitative value is the fluorescence intensity value.

The big-data analyzing method according to the present invention can also be used for an analysis of various kinds of image data, such as the mass spectrometric imaging image, radiographic image or fluorescence image. In these applications, the variable value is the two-dimensional position information on the image, while the quantitative value is a signal intensity value at a predetermined mass-to-charge ratio, X-ray wavelength, fluorescence wavelength or the like. In the case of analyzing a kind of data originating from an animal (inclusive of man), the sex, age or other items of specimen information can be used as the variable value.

The big-data analyzing method according to the present invention can also be used in more common areas of data analyses, including various data analyses commonly known as the "data mining", such as the marketing data analysis, logistics data analysis, data analysis for quality control or abnormality detection, financial data analysis, stock-price data analysis or meteorological data analysis.

For example, in the stock-price data analysis, various enterprises can divided into a plurality of clusters by treating the enterprises as the samples, with the points in time within a predetermined period of time as the variable values and the stock prices as the quantitative values corresponding to the points in time.

It should be noted that the previously described embodiments and their variations are mere examples of the present invention, and any change, modification or addition appropriately made within the spirit of the present invention will naturally fall within the scope of claims of the present application.

REFERENCE SIGNS LIST

1 . . . Mass Spectrometer Main Unit
2 . . . Data Analyzing Unit
21 . . . Spectrum Data Collector
22 . . . Peak Information Extractor
23 . . . Cluster Determiner
24 . . . Cluster Determination Formula Storage Section
3 . . . Operation Unit
4 . . . Display Unit

The invention claimed is:

1. A big-data analyzing method for analyzing data including, as one item of information, quantitative values with respect to a plurality of variable values for each of a plurality of samples, the method comprising:
   determining, for all samples, a degree of similarity between the samples, and a plurality of clusters by grouping samples which are estimated to have comparatively high degrees of similarity into each cluster while excluding a sample which is estimated to have a comparatively low degree of similarity with any of the other samples;
   designating, in each of the plurality of clusters, one or more variable values characterizing the cluster concerned as a marker or markers;
   creating, in each of the plurality of clusters, judgment information for determining whether or not a sample belongs to the cluster concerned based on the marker or markers designated; and
   determining, for a given sample, one or more clusters to which the sample may belong based on the judgment information corresponding to each of the plurality of clusters,
   wherein the plurality of clusters are determined such that a sample pair formed by two samples which are estimated to have a high degree of similarity of data with a high degree of certainty are used as a nucleus, and other samples which are estimated to have a high degree of similarity with one of the two samples are aggregated around the nucleus.

2. The big-data analyzing method according to claim 1, wherein the degree of similarity of the quantitative values corresponding to different variable values in each sample is judged to extract variable values which have a high degree of similarity with each other in the sample, and the sample pair is searched for based on the degree of similarity of the extracted variable values among the samples.

3. The big-data analyzing method according to claim 2, wherein a correlation coefficient is used as an index for measuring the degree of similarity of the quantitative values corresponding to different variable values.

4. The big-data analyzing method according to claim 2, wherein a correlation coefficient is used as an index for measuring the degree of similarity of the quantitative values between the samples.

5. The big-data analyzing method according to claim 1, wherein the degree of similarity is judged for each of the sample pairs formed by all possible combinations of two samples, and a representative sample pair to be used as a new nucleus is designated in descending order of the degree of similarity of the sample pairs under a condition that the sample pair concerned are not a member of any of the clusters already selected as nuclei, while a sample pair having one sample included in a cluster already selected as a nucleus are aggregated into a same group as the representative sample pair to form a core cluster which becomes an origin of a cluster.

6. The big-data analyzing method according to claim 1, wherein in the designating of the marker or markers, a significant-difference test on the quantitative values corresponding to a same variable value is performed between the samples included in one cluster and the samples which are not included in this cluster, and the markers are designated based on the test result.

7. The big-data analyzing method according to claim 5, wherein in each of the core clusters, a plurality of variable values characterizing the core cluster are designated as the markers, and if there are two or more core clusters which have common markers by a proportion equal to or higher than a predetermined value, these two or more core clusters are integrated into one cluster.

8. The big-data analyzing method according to claim 1, wherein whether or not one cluster is a mixture of two other clusters is determined based on a number of markers commonly included in the cluster concerned and in each of the two other clusters.

9. The big-data analyzing method according to claim 1, wherein in the creating of the judgment information, a calculating formula for calculating a sample's probability of being assigned to a cluster by performing a logistic regression analysis on the quantitative values of a plurality of markers designated for the cluster is determined as the judgment information for each cluster.

10. The big-data analyzing method according to claim 1, wherein whether or not a portion or an entirety of the samples included in each cluster belong to the cluster concerned is determined based on the judgment information created in the judgment information creation step, and if there is a sample which is unlikely to belong to the cluster concerned, a process of designating a marker or markers characterizing the cluster concerned and creating the judgment information based on the marker or markers is once more performed after the aforementioned sample is removed from the cluster concerned.

11. The big-data analyzing method according to claim 1, further comprising:
  assigning any sample that is one of all samples yet included in none of the clusters at any stage before an eventual determination of the judgment information to one of the clusters based on the judgment information determined for each cluster.

12. The big-data analyzing method according to claim 3, further comprising:
  calculating the correlation coefficient between all quantitative values corresponding to different variable values for every possible pair of the variable values;
  arranging all correlation coefficients obtained by calculation in order of the value of the correlation coefficient, and calculating the difference between each neighboring pair of the correlation coefficients; and
  sequentially calculating an amount of change in a difference between each neighboring pair of the correlation coefficients in order of the value of the correlation coefficient, and determining a threshold for judging the degree of similarity of the quantitative values based on the amount of change,
  wherein in the determining the degree of similarity and the clusters, the degree of similarity of the quantitative values corresponding to different variable values in each sample is judged using the threshold to extract variable values having a high degree of similarity.

13. The big-data analyzing method according to claim 4, further comprising:
  calculating the correlation coefficient of the variable values between the samples for every possible pair of the samples;
  arranging all correlation coefficients obtained by calculation in order of the value of the correlation coefficient, and calculating a difference between each neighboring pair of the correlation coefficients; and
  sequentially calculating an amount of change in the difference between each neighboring pair of the correlation coefficients in order of the value of the correlation coefficient, and determining a threshold for judging the degree of similarity of the variable values between the samples based on the amount of change,
  wherein in the determining the degree of similarity and the clusters, the degree of similarity of the variable values between the samples is judged using the threshold to extract samples having a high degree of similarity.

14. The big-data analyzing method according to claim 12, wherein in the determining of the threshold, the correlation coefficients are sorted in ascending or descending order and labeled with sort numbers, a correlation-coefficient difference distribution chart having two orthogonally intersecting axes is created, with one axis indicating the sort number and the other axis indicating the difference between two correlation coefficients having consecutive sort numbers, and the threshold is determined based on a correlation coefficient which gives a single correlation-coefficient difference which is outstanding in a direction in which an absolute value of the correlation-coefficient difference increases on the correlation-coefficient difference distribution chart.

15. The big-data analyzing method according to claim 12, wherein in the determining of the threshold, the correlation coefficients are sorted in ascending or descending order and labeled with sort numbers, a correlation-coefficient difference distribution chart having two orthogonally intersecting axes is created, with one axis indicating the sort number and the other axis indicating the difference between two correlation coefficients having consecutive sort numbers, and a correlation coefficient corresponding to the sort number at which the distribution of the correlation-coefficient difference along the axis indicating the sort number exhibits a convex form bulging in a direction in which an absolute value of the correlation-coefficient difference increases is chosen as the threshold.

16. The big-data analyzing method according to claim 15, wherein in the determining of the threshold, the correlation coefficient corresponding to a tip position of the convex portion on the correlation-coefficient difference distribution chart is chosen as the threshold.

17. The big-data analyzing method according to claim 15, wherein in the determining of the threshold, a correlation coefficient corresponding to an extremum of a fitting curve represented by a predetermined function which fits to the convex portion on the correlation-coefficient difference distribution chart is chosen as the threshold.

18. The big-data analyzing method according to claim 15, wherein in the determining of the threshold, whether or not the convex portion is present is determined based on a change in a density of plotted data points on the correlation-coefficient difference distribution chart.

19. The big-data analyzing method according to claim 15, wherein in the determining of the threshold, a correlation coefficient corresponding to a position displaced from the tip position within the convex portion of the distribution of the correlation-coefficient difference on the correlation-coefficient difference distribution chart is chosen as the threshold.

20. The big-data analyzing method according to claim 14, wherein the correlation-coefficient difference distribution chart is displayed on a screen of a display unit.

21. The big-data analyzing method according to claim 15, wherein the correlation-coefficient difference distribution chart is displayed on a screen of a display unit.

22. The big-data analyzing method according to claim 20, wherein the threshold is highlighted on the correlation-coefficient difference distribution chart displayed on the display unit.

23. The big-data analyzing method according to claim 21, wherein the threshold is highlighted on the correlation-coefficient difference distribution chart displayed on the display unit.

24. The big-data analyzing method according to claim 20, wherein the threshold is modified, or the threshold is directly determined, according to a user instruction on the correlation-coefficient difference distribution chart displayed on the display unit.

25. The big-data analyzing method according to claim 14, further comprising:
verifying a determination on an assignment of a sample to a cluster based on a distribution shape on the correlation-coefficient difference distribution chart.

26. The big-data analyzing method according to claim 15, further comprising:
verifying a determination on an assignment of a sample to a cluster based on a distribution shape on the correlation-coefficient difference distribution chart.

27. The big-data analyzing method according to claim 1, wherein the data to be analyzed is a set of mass spectrum data obtained by a mass spectrometric analysis in which the plurality of variable values are mass-to-charge ratio values and the quantitative values are signal intensity values.

28. The big-data analyzing method according to claim 27, wherein the samples are biological samples, and a subtype of a specific kind of cancer is determined by analyzing the mass spectrum data obtained by performing a mass spectrometric analysis on the samples.

29. The big-data analyzing method according to claim 1, wherein the judgment information is a judgement formula.

30. A mass spectrometric system, comprising:
a mass spectrometer configured to perform a mass spectrometric analysis on a target sample to obtain mass spectrum data;
an information storage section in which judgment information is stored;
a data analyzing unit comprising judgement circuitry configured to make a judgment by applying, to the judgment information stored in the information storage section, the mass spectrum data obtained by the mass spectrometer, and configured to determine a cluster which the target sample should be assigned to or yielding information for a determination of the assignment, based on a result of the judgment;
a display unit configured to visually provide users with a process result obtained by the data analyzing unit; and
circuitry configured to execute a big-data analyzing method for analyzing data including, as one item of information, quantitative values with respect to a plurality of variable values for each of a plurality of samples,
wherein the method includes determining, for all samples, a degree of similarity between the samples, and a plurality of clusters by grouping samples which are estimated to have comparatively high degrees of similarity into each cluster while excluding a sample which is estimated to have a comparatively low degree of similarity with any of the other samples, designating, in each of the plurality of clusters, one or more variable values characterizing the cluster concerned as a marker or markers, creating, in each of the plurality of clusters, the judgment information for determining whether or not a sample belongs to the cluster concerned based on the marker or markers designated, and determining, for a given sample, one or more clusters to which the sample may belong based on the judgment information corresponding to each of the plurality of clusters, the data to be analyzed is a set of mass spectrum data obtained by a mass spectrometric analysis in which the plurality of variable values are mass-to-charge ratio values and the quantitative values are signal intensity values, and the plurality of clusters are determined such that a sample pair formed by two samples which are estimated to have a high degree of similarity of data with a high degree of certainty are used as a nucleus, and other samples which are estimated to have a high degree of similarity with one of the two samples are aggregated around the nucleus.

31. The big-data analyzing method according to claim 30, wherein the judgment information is a judgement formula.

* * * * *